(12) United States Patent
Lapidus et al.

(10) Patent No.: US 7,169,560 B2
(45) Date of Patent: Jan. 30, 2007

(54) SHORT CYCLE METHODS FOR SEQUENCING POLYNUCLEOTIDES

(75) Inventors: Stanley N Lapidus, Bedford, NH (US); Philip Richard Buzby, Brockton, MA (US); Timothy Harris, Ocean County, NJ (US)

(73) Assignee: Helicos Biosciences Corporation, Cambridge, MA (US)

( * ) Notice: Subject to any disclaimer, the term of this patent is extended or adjusted under 35 U.S.C. 154(b) by 0 days.

(21) Appl. No.: 10/852,482

(22) Filed: May 24, 2004

(65) Prior Publication Data

US 2005/0100932 A1    May 12, 2005

Related U.S. Application Data

(60) Provisional application No. 60/547,611, filed on Feb. 24, 2004, provisional application No. 60/546,277, filed on Feb. 19, 2004, provisional application No. 60/519,862, filed on Nov. 12, 2003.

(51) Int. Cl.
  *C12Q 1/68*   (2006.01)
  *C07H 21/02*  (2006.01)
  *C07H 21/04*  (2006.01)

(52) U.S. Cl. .................. 435/6; 536/23.1; 536/24.3
(58) Field of Classification Search ............. 435/6; 536/23.1, 24.3
See application file for complete search history.

(56) References Cited

U.S. PATENT DOCUMENTS

| | | |
|---|---|---|
| 3,996,345 A | 12/1976 | Ullman et al. |
| 4,119,368 A | 10/1978 | Yamazaki |
| 4,153,855 A | 5/1979 | Feingold |
| 4,344,064 A | 8/1982 | Bitler et al. |
| 4,351,760 A | 9/1982 | Khanna et al. |
| 4,683,195 A | 7/1987 | Mullis et al. |
| 4,683,202 A | 7/1987 | Mullis |
| 4,707,237 A | 11/1987 | Lepp et al. |
| 4,711,955 A | 12/1987 | Ward et al. |
| 4,725,677 A | 2/1988 | Kosler et al. |
| 4,739,044 A | 4/1988 | Slabinsky |
| 4,757,141 A | 7/1988 | Fung et al. |
| 4,793,705 A | 12/1988 | Shera |
| 4,811,218 A | 3/1989 | Hunkapiller et al. |
| 4,863,849 A | 9/1989 | Melamede |
| 4,865,968 A | 9/1989 | Orgel et al. |
| 4,889,818 A | 12/1989 | Gelfand et al. |
| 4,942,124 A | 7/1990 | Church |
| 4,962,037 A | 10/1990 | Jett et al. |
| 4,971,903 A | 11/1990 | Hyman |
| 4,979,824 A | 12/1990 | Mathies et al. |
| 4,994,368 A | 2/1991 | Goodman et al. |
| 4,994,372 A | 2/1991 | Tabor et al. |
| 4,994,373 A | 2/1991 | Stavrianopoulos et al. |
| 5,085,562 A | 2/1992 | Van Lintel |
| 5,091,652 A | 2/1992 | Mathies et al. |
| 5,096,388 A | 3/1992 | Weinberg |
| 5,096,554 A | 3/1992 | Chin et al. |
| 5,108,892 A | 4/1992 | Burke et al. |
| 5,112,736 A | 5/1992 | Caldwell et al. |
| RE34,069 E | 9/1992 | Kosler et al. |
| 5,143,854 A | 9/1992 | Pirrung et al. |
| 5,167,784 A | 12/1992 | Noolandi |
| 5,171,132 A | 12/1992 | Miyazaki et al. |
| 5,198,540 A | 3/1993 | Koster |
| 5,209,834 A | 5/1993 | Shera |
| 5,224,843 A | 7/1993 | Van Lintel |
| 5,242,797 A | 9/1993 | Hirschfeld |
| 5,259,737 A | 11/1993 | Kamisuki et al. |
| 5,260,433 A | 11/1993 | Engelhardt et al. |
| 5,265,327 A | 11/1993 | Faris et al. |
| 5,267,152 A | 11/1993 | Yang et al. |
| 5,302,509 A | 4/1994 | Cheeseman |
| 5,304,487 A | 4/1994 | Wilding et al. |
| 5,306,403 A | 4/1994 | Vo-Dinh |
| 5,336,062 A | 8/1994 | Richter |
| 5,360,523 A | 11/1994 | Middendorf et al. |
| 5,375,979 A | 12/1994 | Trah |
| 5,376,252 A | 12/1994 | Ekstrom et al. |
| 5,403,709 A | 4/1995 | Agrawal et al. |
| 5,405,747 A | 4/1995 | Ieu et al. |
| 5,405,783 A | 4/1995 | Pirrung et al. |
| 5,409,811 A | 4/1995 | Tabor et al. |
| 5,424,186 A | 6/1995 | Fodor et al. |
| 5,449,767 A | 9/1995 | Ward et al. |

(Continued)

FOREIGN PATENT DOCUMENTS

| | | |
|---|---|---|
| EP | 0579997 A1 | 1/1994 |
| EP | 0703364 | 3/1996 |
| EP | 0706004 A2 | 4/1996 |
| EP | 0779436 A2 | 6/1997 |
| EP | 0845603 | 6/1998 |
| EP | 0932700 B1 | 8/1999 |
| EP | 0946752 B1 | 10/1999 |
| EP | 0955085 A2 | 11/1999 |
| EP | 0999055 A2 | 5/2000 |
| EP | 0706004 B1 | 8/2003 |

(Continued)

OTHER PUBLICATIONS

Canard, et al., "DNA polymerase fluorescent substrates with reversible 3'-tags". Gene, 1994. 148(1): p. 1-6.

Cheng et al., "High-speed DNA sequence analysis," *Prog. in Biochem. and Biophys.*, vol. 22, pp. 223-227 (1995).

(Continued)

*Primary Examiner*—Ethan Whisenant
(74) *Attorney, Agent, or Firm*—Thomas C. Meyers, Esq.; Goodwin Procter LLP

(57) ABSTRACT

The invention provides methods for sequencing a polynucleotide comprising stopping an extension cycle in a sequence by synthesis reaction before the reaction has run to near or full completion.

12 Claims, 9 Drawing Sheets
(7 of 9 Drawing Sheet(s) Filed in Color)

U.S. PATENT DOCUMENTS

| | | |
|---|---|---|
| 5,476,928 A | 12/1995 | Ward et al. |
| 5,484,701 A | 1/1996 | Cocuzza et al. |
| 5,492,806 A | 2/1996 | Drmanac et al. |
| 5,514,256 A | 5/1996 | Douthart et al. |
| 5,518,900 A | 5/1996 | Nikiforov et al. |
| 5,525,464 A | 6/1996 | Drmanac et al. |
| 5,529,465 A | 6/1996 | Zengerle et al. |
| 5,534,125 A | 7/1996 | Middendorf et al. |
| 5,547,839 A | 8/1996 | Dower et al. |
| 5,556,790 A | 9/1996 | Pettit |
| 5,558,991 A | 9/1996 | Trainor |
| 5,599,695 A | 2/1997 | Pease et al. |
| 5,610,287 A | 3/1997 | Nikiforov et al. |
| 5,631,734 A | 5/1997 | Stern et al. |
| 5,632,957 A | 5/1997 | Heller et al. |
| 5,654,149 A | 8/1997 | Mendoza et al. |
| 5,659,171 A | 8/1997 | Young et al. |
| 5,670,346 A | 9/1997 | Reeve et al. |
| 5,674,716 A | 10/1997 | Tabor et al. |
| 5,675,155 A | 10/1997 | Pentoney, Jr. et al. |
| 5,688,648 A | 11/1997 | Mathies et al. |
| 5,695,940 A | 12/1997 | Drmanac et al. |
| 5,705,018 A | 1/1998 | Hartley |
| 5,707,506 A | 1/1998 | Douthart et al. |
| 5,710,628 A | 1/1998 | Waterhouse et al. |
| 5,712,476 A | 1/1998 | Renfrew et al. |
| 5,733,729 A | 3/1998 | Lipshutz et al. |
| 5,741,640 A | 4/1998 | FuBer |
| 5,741,644 A | 4/1998 | Kambara et al. |
| 5,744,305 A | 4/1998 | Fodor et al. |
| 5,744,312 A | 4/1998 | Mamone et al. |
| 5,750,341 A | 5/1998 | Macevicz et al. |
| 5,753,788 A | 5/1998 | Fodor et al. |
| 5,755,943 A | 5/1998 | Middendorf et al. |
| 5,756,285 A | 5/1998 | Fuller |
| 5,759,014 A | 6/1998 | Van Lintel |
| 5,759,374 A | 6/1998 | Takahashi et al. |
| 5,762,876 A | 6/1998 | Lincoln et al. |
| 5,776,767 A | 7/1998 | Stevens et al. |
| 5,776,782 A | 7/1998 | Tsuji |
| 5,789,168 A | 8/1998 | Leushner et al. |
| 5,795,722 A | 8/1998 | Lacroix et al. |
| 5,795,782 A | 8/1998 | Church et al. |
| 5,807,679 A | 9/1998 | Kamb |
| 5,830,657 A | 11/1998 | Leushner et al. |
| 5,831,070 A | 11/1998 | Pease et al. |
| 5,832,165 A | 11/1998 | Reichert et al. |
| 5,834,758 A | 11/1998 | Trulson et al. |
| 5,836,750 A | 11/1998 | Cabuz |
| 5,837,832 A | 11/1998 | Chee et al. |
| 5,837,860 A | 11/1998 | Anderson et al. |
| 5,846,396 A | 12/1998 | Zanzucchi et al. |
| 5,846,727 A | 12/1998 | Soper et al. |
| 5,853,979 A | 12/1998 | Green et al. |
| 5,858,671 A | 1/1999 | Jones |
| 5,861,287 A | 1/1999 | Metzker et al. |
| 5,863,722 A | 1/1999 | Brenner |
| 5,872,244 A | 2/1999 | Hiatt et al. |
| 5,876,187 A | 3/1999 | Afromowitz |
| 5,876,934 A | 3/1999 | Duthie et al. |
| 5,882,904 A | 3/1999 | Riedl et al. |
| 5,885,813 A | 3/1999 | Davis et al. |
| 5,889,165 A | 3/1999 | Fodor et al. |
| 5,902,723 A | 5/1999 | Dower et al. |
| 5,908,755 A | 6/1999 | Kumar et al. |
| 5,916,747 A | 6/1999 | Gilchrist et al. |
| 5,922,591 A | 7/1999 | Anderson et al. |
| 5,922,608 A | 7/1999 | Farnsworth et al. |
| 5,928,906 A | 7/1999 | Koster et al. |
| 5,928,919 A | 7/1999 | Reha-Krantz et al. |
| 5,945,283 A | 8/1999 | Kwok et al. |
| 5,945,284 A | 8/1999 | Livak et al. |
| 5,945,312 A | 8/1999 | Goodman et al. |
| 5,945,325 A | 8/1999 | Arnold et al. |
| 5,948,614 A | 9/1999 | Chatterjee |
| 5,952,174 A | 9/1999 | Nikiforov et al. |
| 5,954,932 A | 9/1999 | Takahashi et al. |
| 5,958,703 A | 9/1999 | Dower et al. |
| 5,959,781 A | 9/1999 | Kintz et al. |
| 5,959,837 A | 9/1999 | Yu |
| 5,965,446 A | 10/1999 | Ishikawa |
| 5,968,740 A | 10/1999 | Fodor et al. |
| 5,974,164 A | 10/1999 | Chee |
| 5,976,338 A | 11/1999 | Fujita et al. |
| 5,981,186 A | 11/1999 | Gabe et al. |
| 5,981,956 A | 11/1999 | Stern |
| 5,994,058 A | 11/1999 | Senapathy |
| 5,994,085 A | 11/1999 | Cantor |
| 6,002,471 A | 12/1999 | Quake |
| 6,005,663 A | 12/1999 | Waterhouse et al. |
| 6,007,309 A | 12/1999 | Hartley |
| 6,015,714 A | 1/2000 | Baldarelli et al. |
| 6,017,702 A | 1/2000 | Lee et al. |
| 6,018,041 A | 1/2000 | Drmanac et al. |
| 6,020,457 A | 2/2000 | Klimash et al. |
| 6,024,925 A | 2/2000 | Little et al. |
| 6,025,136 A | 2/2000 | Drmanac |
| 6,028,190 A | 2/2000 | Mathies et al. |
| 6,030,782 A | 2/2000 | Anderson et al. |
| 6,043,080 A | 3/2000 | Lipshutz et al. |
| 6,046,005 A | 4/2000 | Ju et al. |
| 6,049,380 A | 4/2000 | Goodwin et al. |
| 6,051,380 A | 4/2000 | Sosnowski et al. |
| 6,066,454 A | 5/2000 | Lipshutz et al. |
| 6,071,394 A | 6/2000 | Cheng et al. |
| 6,077,664 A | 6/2000 | Slater et al. |
| 6,077,674 A | 6/2000 | Schleifer et al. |
| 6,087,095 A | 7/2000 | Rosenthal et al. |
| 6,087,099 A | 7/2000 | Gupte et al. |
| 6,094,274 A | 7/2000 | Yokoi |
| 6,107,032 A | 8/2000 | Kilger et al. |
| 6,107,044 A | 8/2000 | Nikiforov |
| 6,132,580 A | 10/2000 | Mathies et al. |
| 6,133,436 A | 10/2000 | Koster et al. |
| 6,136,212 A | 10/2000 | Mastrangelo et al. |
| 6,136,962 A | 10/2000 | Shi et al. |
| 6,140,053 A | 10/2000 | Koster |
| 6,140,494 A | 10/2000 | Hamilton et al. |
| 6,141,096 A | 10/2000 | Stern et al. |
| 6,143,151 A | 11/2000 | Middendorf et al. |
| 6,147,205 A | 11/2000 | McGall et al. |
| 6,156,501 A | 12/2000 | McGall et al. |
| 6,165,694 A | 12/2000 | Liu |
| 6,177,249 B1 | 1/2001 | Kwok et al. |
| 6,197,506 B1 | 3/2001 | Fodor et al. |
| 6,197,595 B1 | 3/2001 | Anderson et al. |
| 6,207,381 B1 | 3/2001 | Larsson et al. |
| 6,207,960 B1 | 3/2001 | Stern |
| 6,210,896 B1 | 4/2001 | Chan |
| 6,214,246 B1 | 4/2001 | Craighead |
| 6,221,592 B1 | 4/2001 | Schwartz et al. |
| 6,221,654 B1 | 4/2001 | Quake et al. |
| 6,225,052 B1 | 5/2001 | Batz et al. |
| 6,225,062 B1 | 5/2001 | Dunn et al. |
| 6,225,092 B1 | 5/2001 | Kilger et al. |
| 6,225,109 B1 | 5/2001 | Juncosa et al. |
| 6,225,567 B1 | 5/2001 | Kester |
| 6,225,625 B1 | 5/2001 | Pirrung et al. |
| 6,228,593 B1 | 5/2001 | Lipshutz et al. |
| 6,232,075 B1 | 5/2001 | Williams |
| 6,232,103 B1 | 5/2001 | Short |
| 6,235,473 B1 | 5/2001 | Friedman et al. |
| 6,242,180 B1 | 6/2001 | Chee |
| 6,242,528 B1 | 6/2001 | Clark et al. |

| Patent No. | Date | Inventor |
|---|---|---|
| 6,245,506 B1 | 6/2001 | Laugharn, Jr. et al. |
| 6,245,507 B1 | 6/2001 | Bogdanov |
| 6,245,518 B1 | 6/2001 | Baier |
| 6,251,610 B1 | 6/2001 | Gupte et al. |
| 6,255,083 B1 | 7/2001 | Williams |
| 6,255,475 B1 | 7/2001 | Kwiatkowski |
| 6,258,533 B1 | 7/2001 | Jones |
| 6,261,776 B1 | 7/2001 | Pirrung et al. |
| 6,261,848 B1 | 7/2001 | Anderson et al. |
| 6,262,838 B1 | 7/2001 | Montagu |
| 6,263,286 B1 | 7/2001 | Gilmanshin et al. |
| 6,268,152 B1 | 7/2001 | Fodor et al. |
| 6,268,219 B1 | 7/2001 | Mcbride et al. |
| 6,269,846 B1 | 8/2001 | Overbeck et al. |
| 6,270,644 B1 | 8/2001 | Mathies et al. |
| 6,270,961 B1 | 8/2001 | Drmanac |
| 6,274,320 B1 | 8/2001 | Rothberg et al. |
| 6,274,351 B1 | 8/2001 | Peponnet |
| 6,277,604 B1 | 8/2001 | Peponnet |
| 6,280,954 B1 | 8/2001 | Ulfendahl |
| 6,284,460 B1 | 9/2001 | Fodor et al. |
| 6,287,821 B1 | 9/2001 | Shi et al. |
| 6,294,336 B1 | 9/2001 | Boyce-Jacino et al. |
| 6,294,337 B1 | 9/2001 | Hayashizaki |
| 6,306,607 B2 | 10/2001 | Williams |
| 6,309,601 B1 | 10/2001 | Juncosa et al. |
| 6,309,701 B1 | 10/2001 | Barbera-Guillem |
| 6,309,824 B1 | 10/2001 | Drmanac |
| 6,309,836 B1 | 10/2001 | Kwiatkowski |
| 6,309,886 B1 | 10/2001 | Ambrose et al. |
| 6,310,189 B1 | 10/2001 | Fodor et al. |
| 6,312,893 B1 | 11/2001 | Van Ness et al. |
| 6,316,191 B1 | 11/2001 | Drmanac et al. |
| 6,322,968 B1 | 11/2001 | Head et al. |
| 6,331,439 B1 | 12/2001 | Cherukuri et al. |
| 6,333,183 B1 | 12/2001 | Evans et al. |
| 6,335,824 B1 | 1/2002 | Overbeck |
| 6,337,185 B1 | 1/2002 | Asp et al. |
| 6,337,188 B1 | 1/2002 | Head et al. |
| 6,342,326 B1 | 1/2002 | Milton |
| 6,344,325 B1 | 2/2002 | Quake et al. |
| 6,346,379 B1 | 2/2002 | Gelfand et al. |
| 6,346,413 B1 | 2/2002 | Fodor et al. |
| 6,355,420 B1 | 3/2002 | Chao |
| 6,355,432 B1 | 3/2002 | Fodor et al. |
| 6,361,671 B1 | 3/2002 | Mathies et al. |
| 6,361,937 B1 | 3/2002 | Stryer |
| 6,368,562 B1 | 4/2002 | Yao |
| 6,368,699 B1 | 4/2002 | Gilbert et al. |
| 6,383,749 B2 * | 5/2002 | Bochkariov et al. ............ 435/6 |
| 6,387,626 B1 | 5/2002 | Shi et al. |
| 6,395,232 B1 | 5/2002 | McBride |
| 6,395,559 B1 | 5/2002 | Swenson |
| 6,397,150 B1 | 5/2002 | Izmailov |
| 6,399,364 B1 | 6/2002 | Reeve et al. |
| 6,401,267 B1 | 6/2002 | Drmanac |
| 6,403,311 B1 | 6/2002 | Chao |
| 6,403,315 B1 | 6/2002 | Drmanac |
| 6,403,317 B1 | 6/2002 | Anderson |
| 6,403,320 B1 | 6/2002 | Read et al. |
| 6,403,957 B1 | 6/2002 | Fodor et al. |
| 6,404,907 B1 | 6/2002 | Gilchrist et al. |
| 6,406,893 B1 | 6/2002 | Knapp et al. |
| 6,407,858 B1 | 6/2002 | Montagu |
| 6,416,952 B1 | 7/2002 | Pirrunll et al. |
| 6,420,169 B1 | 7/2002 | Read et al. |
| 6,423,273 B1 | 7/2002 | O'Mara |
| 6,432,634 B1 | 8/2002 | Digby et al. |
| 6,436,641 B1 | 8/2002 | Izmailov |
| 6,436,646 B1 | 8/2002 | Nikiforov |
| 6,440,664 B1 | 8/2002 | Digby et al. |
| 6,440,772 B1 | 8/2002 | Knapp et al. |
| 6,444,106 B1 | 9/2002 | Mcbride et al. |
| 6,444,173 B1 | 9/2002 | Sjursen et al. |
| 6,444,424 B1 | 9/2002 | Chatterjee et al. |
| 6,444,461 B1 | 9/2002 | Knapp et al. |
| 6,447,724 B1 | 9/2002 | Jensen et al. |
| 6,448,090 B1 | 9/2002 | McBride |
| 6,451,536 B1 | 9/2002 | Fodor et al. |
| 6,479,267 B1 | 11/2002 | Davis et al. |
| 6,485,690 B1 | 11/2002 | Pfost et al. |
| 6,485,909 B1 | 11/2002 | Hong et al. |
| 6,485,944 B1 | 11/2002 | Church et al. |
| 6,495,363 B2 | 12/2002 | Bogdanov |
| 6,506,560 B1 | 1/2003 | Hughes et al. |
| 6,511,803 B1 | 1/2003 | Church et al. |
| 6,514,706 B1 | 2/2003 | Von Kalle et al. |
| 6,521,428 B1 | 2/2003 | Senapathy |
| 6,524,829 B1 | 2/2003 | Seeger |
| 6,528,258 B1 | 3/2003 | Russell |
| 6,528,288 B2 | 3/2003 | Senapathy |
| 6,537,755 B1 | 3/2003 | Drmanac |
| 6,537,757 B1 | 3/2003 | Langmore et al. |
| 6,546,340 B2 | 4/2003 | Lipshutz et al. |
| 6,551,784 B2 | 4/2003 | Fodor et al. |
| 6,551,817 B2 | 4/2003 | Besemer et al. |
| 6,554,987 B1 | 4/2003 | Gilchrist et al. |
| 6,555,349 B1 | 4/2003 | O'Donnell |
| 6,558,945 B1 | 5/2003 | Kao |
| 6,562,566 B1 | 5/2003 | Hoheisel |
| 6,566,059 B1 | 5/2003 | Stanton, Jr. et al. |
| 6,566,515 B1 | 5/2003 | McGall et al. |
| 6,573,047 B1 | 6/2003 | Hung et al. |
| 6,573,374 B1 | 6/2003 | Muehleger et al. |
| 6,576,424 B2 | 6/2003 | Fodor et al. |
| 6,576,425 B2 | 6/2003 | McGall et al. |
| 6,579,704 B2 | 6/2003 | Short |
| 6,582,923 B2 | 6/2003 | Stanton, Jr. et al. |
| 6,585,939 B1 | 7/2003 | Dapprich |
| 6,607,888 B2 | 8/2003 | Schwartz et al. |
| 6,610,482 B1 | 8/2003 | Fodor et al. |
| 6,613,513 B1 | 9/2003 | Parco et al. |
| 6,623,928 B2 | 9/2003 | Van Ness et al. |
| 6,627,748 B1 | 9/2003 | Ju et al. |
| 6,642,001 B1 | 11/2003 | Bolk et al. |
| 6,664,079 B2 | 12/2003 | Ju et al. |
| 6,719,868 B1 | 4/2004 | Schueller et al. |
| 6,750,018 B2 | 6/2004 | Kambara et al. |
| 6,783,938 B2 | 8/2004 | Nygren et al. |
| 6,787,308 B2 | 9/2004 | Balasubramanian et al. |
| 2001/0024790 A1 | 9/2001 | Kambara et al. |
| 2001/0044531 A1 | 11/2001 | McGall et al. |
| 2001/0046681 A1 | 11/2001 | Senapathy |
| 2002/0009744 A1 | 1/2002 | Bogdanov |
| 2002/0012910 A1 | 1/2002 | Weiss et al. |
| 2002/0015961 A1 | 2/2002 | Kwiatkowski |
| 2002/0025529 A1 | 2/2002 | Quake et al. |
| 2002/0032320 A1 | 3/2002 | Burgess et al. |
| 2002/0034792 A1 | 3/2002 | Kilger et al. |
| 2002/0039738 A1 | 4/2002 | Williams et al. |
| 2002/0042112 A1 | 4/2002 | Koster et al. |
| 2002/0045182 A1 | 4/2002 | Singh et al. |
| 2002/0051992 A1 | 5/2002 | Bridgham et al. |
| 2002/0053532 A1 | 5/2002 | Quake et al. |
| 2002/0061529 A1 | 5/2002 | Bridgham et al. |
| 2002/0072055 A1 | 6/2002 | Jones |
| 2002/0086318 A1 | 7/2002 | Manalis et al. |
| 2002/0102586 A1 | 8/2002 | Ju et al. |
| 2002/0102595 A1 | 8/2002 | Davis |
| 2002/0106673 A1 | 8/2002 | Drmanac et al. |
| 2002/0115076 A1 | 8/2002 | Williams |
| 2002/0115092 A1 | 8/2002 | Rebek, Jr. |
| 2002/0119484 A1 | 8/2002 | Weidenhammer et al. |
| 2002/0123046 A1 | 9/2002 | Smith et al. |
| 2002/0137046 A1 | 9/2002 | Koster |
| 2002/0137052 A1 | 9/2002 | Bridgham et al. |

| | | | | | | |
|---|---|---|---|---|---|---|
| 2002/0137062 A1 | 9/2002 | Williams et al. | | WO | 93/06121 A1 | 4/1993 |
| 2002/0138205 A1 | 9/2002 | Miller et al. | | WO | 93/21340 A1 | 10/1993 |
| 2002/0142329 A1 | 10/2002 | Matray et al. | | WO | 95/12608 A1 | 5/1995 |
| 2002/0142333 A1 | 10/2002 | Gelfand et al. | | WO | 95/27080 A1 | 10/1995 |
| 2002/0146704 A1 | 10/2002 | Head et al. | | WO | 96/04547 A1 | 2/1996 |
| 2002/0146726 A1 | 10/2002 | Matray et al. | | WO | 96/12014 A1 | 4/1996 |
| 2002/0150903 A1 | 10/2002 | Koster | | WO | 96/12039 | 4/1996 |
| 2002/0150938 A1 | 10/2002 | Kneipp et al. | | WO | 96/27025 | 9/1996 |
| 2002/0164629 A1 | 11/2002 | Quake et al. | | WO | 97/02488 | 1/1997 |
| 2002/0168642 A1 | 11/2002 | Drukier | | WO | 97/22076 | 6/1997 |
| 2002/0168678 A1 | 11/2002 | Williams et al. | | WO | 97/23650 | 6/1997 |
| 2002/0172948 A1 | 11/2002 | Perlin | | WO | 97/37041 | 10/1997 |
| 2002/0177129 A1 | 11/2002 | Paabo et al. | | WO | 97/39150 | 10/1997 |
| 2002/0182601 A1 | 12/2002 | Sampson et al. | | WO | 97/40184 | 10/1997 |
| 2002/0192661 A1 | 12/2002 | Paabo et al. | | WO | 97/41258 | 11/1997 |
| 2002/0192662 A1 | 12/2002 | Boyce-Jacino et al. | | WO | 97/41259 | 11/1997 |
| 2002/0192691 A1 | 12/2002 | Drmanac | | WO | 97/42348 | 11/1997 |
| 2002/0197618 A1 | 12/2002 | Sampson | | WO | 98/00708 | 1/1998 |
| 2003/0003498 A1 | 1/2003 | Digby et al. | | WO | 98/02575 | 1/1998 |
| 2003/0008285 A1 | 1/2003 | Fischer | | WO | 98/03684 | 1/1998 |
| 2003/0017461 A1 | 1/2003 | Singh et al. | | WO | 98/07069 | 2/1998 |
| 2003/0022207 A1 | 1/2003 | Balasubramanian et al. | | WO | 98/13523 A1 | 4/1998 |
| 2003/0027140 A1 | 2/2003 | Ju et al. | | WO | 98/08978 | 5/1998 |
| 2003/0036080 A1 | 2/2003 | Jensen et al. | | WO | 98/20019 | 5/1998 |
| 2003/0044778 A1 | 3/2003 | Goelet et al. | | WO | 98/20020 A2 | 5/1998 |
| 2003/0044779 A1 | 3/2003 | Goelet et al. | | WO | 98/20166 | 5/1998 |
| 2003/0044781 A1 | 3/2003 | Korlach et al. | | WO | 98/21361 | 5/1998 |
| 2003/0044816 A1 | 3/2003 | Denison et al. | | WO | 98/27228 | 6/1998 |
| 2003/0054181 A1 | 3/2003 | Swerdlow et al. | | WO | 98/28440 A1 | 7/1998 |
| 2003/0054361 A1 | 3/2003 | Heller | | WO | 98/33939 A1 | 8/1998 |
| 2003/0058440 A1 | 3/2003 | Scott et al. | | WO | 98/40520 | 9/1998 |
| 2003/0058799 A1 | 3/2003 | Yamakawa et al. | | WO | 98/41650 | 9/1998 |
| 2003/0059778 A1 | 3/2003 | Berlin et al. | | WO | 98/41657 A1 | 9/1998 |
| 2003/0060431 A1 | 3/2003 | Simmonds et al. | | WO | 98/44152 | 10/1998 |
| 2003/0064366 A1 | 4/2003 | Hardin et al. | | WO | 98/45481 A1 | 10/1998 |
| 2003/0064398 A1 | 4/2003 | Barnes | | WO | 98/53300 | 11/1998 |
| 2003/0064483 A1 | 4/2003 | Shaw et al. | | WO | 98/54669 | 12/1998 |
| 2003/0087237 A1 | 5/2003 | Hong et al. | | WO | 98/55593 | 12/1998 |
| 2003/0087300 A1 | 5/2003 | Knapp et al. | | WO | 99/01768 | 1/1999 |
| 2003/0092005 A1 | 5/2003 | Levene et al. | | WO | 99/05221 | 2/1999 |
| 2003/0092007 A1 | 5/2003 | Gibbs et al. | | WO | 99/05315 A2 | 2/1999 |
| 2003/0096258 A1 | 5/2003 | Fu et al. | | WO | 99/06422 | 2/1999 |
| 2003/0100006 A1 | 5/2003 | Senapathy | | WO | 99/13109 | 3/1999 |
| 2003/0104437 A1 | 6/2003 | Barnes et al. | | WO | 99/13110 | 3/1999 |
| 2003/0104466 A1 | 6/2003 | Knapp et al. | | WO | 99/17093 | 4/1999 |
| 2003/0108867 A1 | 6/2003 | Chee et al. | | WO | 99/19516 | 4/1999 |
| 2003/0138809 A1 | 7/2003 | Williams et al. | | WO | 99/24797 | 5/1999 |
| 2003/0148344 A1 | 8/2003 | Rothberg et al. | | WO | 99/27137 A1 | 6/1999 |
| 2003/0162213 A1 | 8/2003 | Fuller et al. | | WO | 99/31278 | 6/1999 |
| 2003/0186227 A1 | 10/2003 | Balasubramanian et al. | | WO | 99/37810 A1 | 7/1999 |
| 2003/0186255 A1 | 10/2003 | Williams et al. | | WO | 99/39001 | 8/1999 |
| 2003/0190627 A1 | 10/2003 | Zhao et al. | | WO | 99/40105 A2 | 8/1999 |
| 2003/0190647 A1 | 10/2003 | Odera | | WO | 99/40223 | 8/1999 |
| 2003/0190663 A1 | 10/2003 | Yang et al. | | WO | 99/41410 | 8/1999 |
| 2003/0194722 A1 | 10/2003 | Odedra et al. | | WO | 99/44045 | 9/1999 |
| 2003/0194740 A1 | 10/2003 | Williams | | WO | 99/45153 | 9/1999 |
| 2004/0009487 A1 | 1/2004 | Kadushin et al. | | WO | 99/47539 | 9/1999 |
| 2004/0029115 A9 | 2/2004 | Dower et al. | | WO | 99/47706 | 9/1999 |
| 2004/0054162 A1 | 3/2004 | Hanna | | WO | 99/53423 | 10/1999 |
| 2004/0106110 A1 | 6/2004 | Balasubramanian et al. | | WO | 99/61888 A2 | 12/1999 |
| 2004/0126770 A1 | 7/2004 | Kumar et al. | | WO | 99/64437 | 12/1999 |
| | | | | WO | 99/64840 | 12/1999 |
| | FOREIGN PATENT DOCUMENTS | | | WO | 99/65938 | 12/1999 |
| | | | | WO | 99/66076 A1 | 12/1999 |
| GB | 2155152 | 9/1985 | | WO | 99/66313 A1 | 12/1999 |
| GB | 2308460 | 6/1997 | | WO | 00/00637 | 1/2000 |
| GB | 2400518 A | 10/2004 | | WO | 00/06770 A1 | 2/2000 |
| SE | 9500589-8 | 2/1995 | | WO | 00/09753 | 2/2000 |
| WO | 90/13666 A1 | 11/1990 | | WO | 00/11223 A1 | 3/2000 |
| WO | 90/15070 A1 | 12/1990 | | WO | 00/17397 | 3/2000 |
| WO | 91/06678 A1 | 5/1991 | | WO | 00/26935 A2 | 5/2000 |
| WO | 92/10092 A1 | 6/1992 | | WO | 00/34523 A1 | 6/2000 |
| WO | 92/10587 A1 | 6/1992 | | WO | 00/37680 A1 | 6/2000 |

| | | | |
|---|---|---|---|
| WO | 00/40750 A1 | 7/2000 | |
| WO | 00/40758 | 7/2000 | |
| WO | 00/42223 | 7/2000 | |
| WO | 00/43540 A1 | 7/2000 | |
| WO | 00/43752 | 7/2000 | |
| WO | 00/50642 A1 | 8/2000 | |
| WO | 00/53805 A1 | 9/2000 | |
| WO | 00/53812 A2 | 9/2000 | |
| WO | 00/56937 | 9/2000 | |
| WO | 00/58507 A1 | 10/2000 | |
| WO | 00/58516 A2 | 10/2000 | |
| WO | 00/68410 | 11/2000 | |
| WO | 00/70073 A1 | 11/2000 | |
| WO | 00/71755 | 11/2000 | |
| WO | 00/79007 | 12/2000 | |
| WO | 01/001025 A3 | 1/2001 | |
| WO | 01/16375 | 3/2001 | |
| WO | 01/23610 A2 | 4/2001 | |
| WO | 01/24937 A2 | 4/2001 | |
| WO | 01/25480 | 4/2001 | |
| WO | 01/31055 A2 | 5/2001 | |
| WO | 01/32930 A1 | 5/2001 | |
| WO | 01/38574 | 5/2001 | |
| WO | 01/48184 A2 | 5/2001 | |
| WO | 01/42496 A2 | 6/2001 | |
| WO | 01/57248 A2 | 8/2001 | |
| WO | 01/57249 A1 | 8/2001 | |
| WO | 01/61044 | 8/2001 | |
| WO | 01/64838 | 9/2001 | |
| WO | 01/75154 | 10/2001 | |
| WO | 01/79536 | 10/2001 | |
| WO | 01/85991 | 11/2001 | |
| WO | 01/92284 | 12/2001 | |
| WO | 01/96607 | 12/2001 | |
| WO | 02/00343 A2 | 1/2002 | |
| WO | 02/02584 | 1/2002 | |
| WO | 02/02795 | 1/2002 | |
| WO | 02/002795 | 1/2002 | |
| WO | 02/02813 A2 | 1/2002 | |
| WO | 02/03305 A2 | 1/2002 | |
| WO | 02/04680 A2 | 1/2002 | |
| WO | 02/20836 | 3/2002 | |
| WO | 02/20837 A2 | 3/2002 | |
| WO | 02/27032 | 4/2002 | |
| WO | 02/29106 A2 | 4/2002 | |
| WO | 02/030486 A3 | 4/2002 | |
| WO | 02/35441 A2 | 5/2002 | |
| WO | 02/36832 | 5/2002 | |
| WO | 02/44414 | 6/2002 | |
| WO | 02/061126 A2 | 8/2002 | |
| WO | 02/061127 A2 | 8/2002 | |
| WO | 02/072779 A2 | 9/2002 | |
| WO | 02/072892 A1 | 9/2002 | |
| WO | 02/077694 | 10/2002 | |
| WO | 02/079519 | 10/2002 | |
| WO | 02/088381 A2 | 11/2002 | |
| WO | 02/088382 A2 | 11/2002 | |
| WO | 02/097113 | 12/2002 | |
| WO | 02/099398 | 12/2002 | |
| WO | 03/002767 | 1/2003 | |
| WO | 03/016565 A2 | 2/2003 | |
| WO | 03/020968 A2 | 3/2003 | |
| WO | 03/021010 | 3/2003 | |
| WO | 03/031947 A2 | 4/2003 | |
| WO | 03/044678 | 5/2003 | |
| WO | 03/048178 | 6/2003 | |
| WO | 03/048991 | 6/2003 | |
| WO | 03/062897 | 7/2003 | |
| WO | 04/061119 | 7/2004 | |
| WO | 04/074503 | 9/2004 | |

OTHER PUBLICATIONS

Decher et al., "Buildup of ultrathin multilayer films by a self-assembly process," Thin Solid Films, 210/211:831-835 (1992).

Driscoll et al., "Atomic-Scale Imaging of DNA Using Scanning Tunneling Microscopy." Nature, 1990.346(6281): p. 294-296.

Felicia, Y. et al., "Synthesis and Properties of Adenosine-5'-triphosphoro-y-l-(5-sulfonic acid)naphthyl Ethylamidate: A Fluorescent Nucleotide Substrate for DNA-Dependent RNA Polymerase from E. colt", Arch. Biochem. Biophys., 246(2):564-571 (1986).

Goodwin, P.M., et al., "Application of single molecule detection to DNA sequencing." Nucleosides & Nucleotides, 1997. 16(5-6): p. 543-550.

Gravesen et al., "Microfluidics—a review", J. Micromech. Microeng. 3IOP Publishing Ltd., pp. 168-192 (1993).vol. 3.

Ha, "Single-molecule fluorescence methods for the study of nucleic acids," Current Opinion in Struct Bio, 11, 2001, 287-292.

Ha et al., "Single-molecule fluorescence spectroscopy of enzyme conformational dynamics and cleavage mechanism." Proceedings of the National Academy of Sciences of the United States of America, 1999.96(3): p. 893-898.

Harding et al., "Single-molecule detection as an approach to rapid DNA sequencing," Trends in Biotechnology, vol. 10, 1992.

Howorka, et al., "Sequence-specific detection of individual DNA strands using engineered nanopores." Nature Biotechnology, 2001. 19(7): p. 636-639.

Adam et al., "Individual genomes targeted in sequencing revolution", Nature, vol. 411, p. 402 (May 2001).

Agrawal, S. et al., "Site Specific Functionalization of Oligodeoxynucleotides for Non-Radioactive Labelling", Tetrahedron Letters, vol. 31, No. 11, pp. 1543-1546 (1990).

Ambrose, W. et al., "Single Molecule Detection With Total Internal Reflection Excitation: Comparing Signal-to-Background and Total Signals in Different Geometries", Cytometry, vol. 36, pp. 224-231 (1999).

Amit, B. et al., "Photosensitive Protecting Groups of Amino Sugars and Their Use in Glycoside Synthesis . . . Derivatives", 1. Org. Chem., 39(2):192-6 (1974).

Arndt-Jovin, D. et al., "Immunofluorescence Localization ofZ-DNA in Chromosomes: Quantitation by Scanning Microphotometry and Computer-assisted Image Analysis", I. Cell Bio!o?JI, vol. 101, pp. 1422-1433, (Oct. 1985).

Augustin, M.A., W. Ankenbauer, and B. Angerer, "Progress towards single-molecule sequencing: enzymatic synthesis of nucleotide-specifically labeled DNA." Journal of Biotechnology, 2001. 8(13): p. 289.

Axelrod, D., "Cell-Substrate Contacts Illuminated by Total Internal Reflection Fluorescence", I. Cell Bio!o?JI, vol. 89, pp. 141-145, (April 1981).

Axelrod, D. et al., "Total internal reflection fluorescent microscopy", J Microscopy, vol. 129, pp. 19-28, (1983).

Bai, X., et al., "Photocleavage of a 2-nitrobenzyl linker bridging a fluorophore to the 5' end of DNA." Proc Natl Acad Sci USA, 2003, vol. 100(2). p. 409-13.

Basche, T. et al., "Single Molecule Optical Detection, Imaging and Spectroscopy", Chs. 2 and 3, Weinheim:VCM, Germany (1997).

Beaucage, S. et al., "Advances in the Synthesis of Oligonucleotides by the Phosphoramidite Approach" Tetrahedron, 48:2223-2311 (1992).

Beese, L. et al., "Structure of DNA Polymerase I Klenow Fragment Bound to Duplex DNA", Science, 260:352-355 (1993).

Bennett et. al., "Solexa Sequencing chemistry can be applied to different platforms which will have common elements in detection and data processing." Pharmacogenomics (2004) 5(4).

Biesalski et al., "Preparation and Characterization of a Polyelectrolyte Monolayer Covalently Attached to a Planar Solid Surface." Macromolecules 111, 32, 2309-2316. Article was published on the web Mar. 10, 1999.

Black, D.L., Protein diversity from alternating splicing: A challenge for bioinformatics and post genome biology. Cell, 2000. 103(3): p. 367-370.

Blattner, F.R., et al., "The Complete genome sequence of Escherichia coli K-12." Science, 1997.277(5331):p. 1453-74.

Boles et. al., "High-Resolution Mapping of Carcinogen Binding Sites on DNA" 1986, 25, 3039-3043.

Brakmann, S. and P. Nieckchen, "The large fragment of Escherichia coli DNA polymerase I can synthesize DNA exclusively from fluorescently labeled nucleotides." Chembiochem, 2001. 2(10):p. 773-777.

Brackmann et. al, "Optimal Enzymes for Single-Molecule Sequencing" 18, D-04103.

Braslavsky, I. et al., "Sequence information can be obtained from single DNA molecules", PNAS, vol. 100, No. 7, pp. 3960-3964 (Apr. 2003).

Braslavsky, I. et al., "Objective-type dark-field illumination for scattering from microbeads", Applied Optics, vol. 40, No. 31, pp. 5650-5657, (Nov. 2001).

Braslavsky, I. et al., "Single Molecule Measurements of DNA Polymerase Activity: A Step Towards Single Molecule Sequencing", Biophys. I. Abstracts, p. 507A (2002).

Brechtel, R. et al., "Control of the electro osmotic flow by metal-salt-containing buffers", J Chromatoraphy A, vol. 716, pp. 97-105, (1995).

Bridgman, A. et al., "An improved method for the synthesis ofmercurated Dutp. Enzymatic synthesis of Hg-labelled DNA of high molecular weight suitable for use in an image based DNA sequencing strategy", DNA Seq., vol. 6, No. 4, pp. 199-209 (1996).

Bryzek, J. etal., "Micromachines on the march", IEEE Spectrum, vol. 31, No. 5, pp. 20-31, (1994).

Buchaillot, L. et al., "Silicon Nitride Thin Films Young's Modulus Determination by an Optical Non Destructive Method", Jpn. J. Appl. Phys., vol. 36, pp. L794-L797, (Jun. 1997).

Burghardt, T. et al., "Total Internal Reflection Fluorescence Study of Energy Transfer in Surface-Adsorbed and Dissolved Bovine Serum Albumin", Biochemistry, vol. 22, pp. 979-985 (1983).

Butler, D. et al. "Draft data leave geneticists with a mountain still to climb", Nature, vol. 405, Issue 6782, pp. 984-985 (May 2000).

Canard, B., B. Cardona, .and R.S. Sarfati, "Catalytic editing properties of DNA polymerases." Proc Natl Acad Sci USA, 1995. 92(24): p. 10859-63.

Chicurel, M., "Faster, better, cheaper genotyping", Nature, vol. 412, Issue 6847, pp. 580-582, (Aug. 2001).

Chidgeavadze, Z. et al., "3'-Fluro-2',3'-dideoxyribonucleoside 5'-triphosphates: terminators of DNA synthesis", FEBS Letters, 183(2):275-278 (1985).

Chiu, D. et al., "Patterned deposition of cells and proteins onto surfaces by using three-dimensional microfluidic systems," PNAS, vol. 97, No. 6, pp. 2408-2413 (2000).

Chou et al., "A microfabricated device for sizing and sorting DNA molecules", Applied Sciences, Biophysics: Chou et al., Proc. Natl. Acad. Sci. USA 96, pp. 11-13 (1999).

Chou et al., "A Microfabricated Rotary Pump". Biomedical Microdevices. vol. 3: p. 323 (2001).

Close, D. et al., "Ultraviolet Photobleaching of Free Radicals Created in y-Irradiated Amino Acids", Radiation Research, vol. 53, pp. 349-357 (1973).

Cooper, J. et al., "Analysis of Fluorescence Energy Transfer in Duplex and Branched DNA Molecules", Biochemistry, vol. 29, pp. 9261-9268 (1990).

Crocker, J.C. and D.G. Grier, "Methods of digital video microscopy for colloidal studies." Journal of Colloid and Interface Science, 1996. 179(1): p. 298-310.

Dapprich, J., "Single-molecule DNA digestion by lambda-exonuclease." Cytometry, 1999.36(3): p. 163-168.

Debenham, J.S., et al., "Two New Orthogonal Amine-Protecting Groups that can be Cleaved under Mild or Neutral Conditions." Journal of the American Chemical Society, 1995. 117(11): p. 3302-3.

Decher, G. et al. "Buildup of ultrathin multiplayer files by a self-assembly process: III. Consecutively alternating absorption of anionic and cationic polyelectrolytes on charged surfaces", Thin Solid Films, 210:831-835 (1992).

Decher G.;et al., "Fuzzy nanoassemblies : Toward layered polymeric multicomposites." Science, 1997.277(5330): p. 1232-1237.

Delamarche, E. et al., "Patterned Delivery of Immunoglobulins to Surfaces Using Microfluidic Networks", Science 276:779-781 (1997).

Dickson et al., "Simultaneous Imaging of Individual Molecules aligned both parallel and perpendicular to the optic axis" vol. 81, No. 24, 1998.

Doktycz, M. et al., "Genosensors and Model Hybridization Studies", Automation Technologies for Genome Characterization, Ch. 10 T. Beugelsdijk (Ed), John Wiley & Sons, Inc. (1997), pp. 205-225.

Doublie, S. et al., "Crystal structure of a bacteriophage T7 DNA replication complex at 2.2 A resolution", Nature; vol. 391, pp. 251-258 (Jan. 1998).

Drmanac, R. et al., "Sequencing by hybridization: Towards an automated sequencing of one million M13 clones arrayed on membranes", Electrophoresis, 13:566-573 (1992).

Duffy et al., "Patterning Electroluminescence Materials with Feature Sizes as Small as 5 um Using Elastomeric Membrains as Masks for Dry Lift-Off," Advanced Materials vol. 11, No. 7, pp. 546-552 (1999).

Duffy et al., "Rapid prototyping of microfludic switches in poly(dimethyl siloxane) and their acuation by electroosmotic flow," J. Micromech. Microeng., (1999) vol., 9, pp. 211-217.

Duffy et al., "Rapid Prototyping of Microfluidic Systems in Poly(dimethylsiloxane)", Analytical Chemistry, vol. 70, No. 23, pp. 4974-4984 (1998).

Effenhauser et al., "Integrated capillary electrophoresis on Flexible silicone microdevices: Analysis of DNA restriction fragments and detection of single DNA molecules on microchips," Anal. Chem., vol. 69, pp. 3451-3457 (1997).

Effenhauser et al., "Integrated chip-based capillary electrophoresis," Electrophoresis, vol. 18, pp. 2203-2213 (1997).

Eigen, M. et al., "Sorting single molecules: Application to diagnostics and evolutionary biotechnology", PNAS, vol. 91, pp. 5740-5747, (Jun. 1994).

Evangelista, R.A., et al. "Characterization of fluorescent nucleoside triphosphates by capillary electrophoresis with laser-induced fluorescence detection: action of alkaline phosphatase and DNA polymerase." Anal Biochem, 1996.235(1): p. 89-97.

Fahrenberg et al., "A microvalve system fabricated by thermoplastic molding," J. Micromech. Microeng., vol. 5, pp. 169-171(1995).

Ferguson, et al., "A fiber-optic DNA biosensor microarray for the analysis of gene expression," Nature Biotechnology, vol. 14, pp. 1681-1684 (1996).

Firtz, I. et al., "Electronic detection of DNA by its intrinsic molecular charge", PNAS, vol. 99, No. 22, pp. 14142-14146 (Oct. 2002).

Forster, T., "Delocalized Excitation and Excitation Transfer", Modem Quantum Chem., Istanbul Lectures, Part TII, pp. 93-137, Academic Press, New York (1965).

Fu et al., "A microfabricated fluorescence-activated cell sorter," Nature Biotechnology, vol. 17, pp. 1109-1111 (1999).

Fu e al., "An integrated microfabricated cell sorter". Anal Cherm, 2002. 74(11): p. 451-7.

Funatsu, T. et al., "Imaging of single fluorescent molecules and individual ATP turnovers by single myosin molecules in aqueous solution", Nature, vol. 374, pp. 555-559 (Apr. 1995).

Garcia, A., "Detennination of Ion Penneability by Fluorescence Quenching", Meth. in Enzimolgy, 207:501-511 (1992).

Gardner et al., "Comparative kinetics of nucleotide analog incorporation by Vent DNA polymerase," J. Biol. Chem., 279, No. 12, Mar. 19, 2004, 11834-11842.

Giller et al., "Incorporation of reporter molecule-labeled nucleotides by DNA polymerases. I. Chemical synthesis of various reporter group-labeled 2'deoxyribonucleoside-5'-triphosphates," Nucleic Acids Res., 31, No. 10, 2003, 2630-2635.

Giusti, W. et al., "Synthesis and Characterization of 5' -Fluorescent-dye-labeled Oligonucleotides", PCR Methods and Applications, 2:223-227 (1993).

Goll et al., "Microvalves with bistable buckled polymer diaphragms," J. Micromech. Microeng., vol. 6., pp. 77-79 (1996).

Greene, T.W. and P.G.M. Wuts, "Protective Groups in Organic Synthesis." John Wiley & Sons, Inc.: New York, 1999 3rd Ed.

Gueroui, Z., et al., "Observation by fluorescence microscopy of transcription on single combed DNA." Proceedings of the National Academy of Sciences of the United States of America, 2002. 99(9): p. 6005-6010.

Guilbault, G., "Practical Fluorescence—Theory, Methods and Techniques," Chapters 1 and 3, and pp. 521-524, Marcel Dekker, Inc., New York (1973).

Gyllenstein, U. et al., "Generation of single-stranded DNA by the polymerase chain reaction and its application to direct sequencing of the HLA-DQA locus", PNAS 85:7652-56.

Ha, "Single molecule dynamics studied by polarization modulation," Phys. Rev. Lett., 77, No. 19, Nov. 4, 1996, 39793982.

Ha, "Single molecule spectroscopy with automated positioning," Appl. Phys. Lett. 70, No. 6, Feb. 10, 1997, 782-784.

Ha, T., "Single-molecue fluorescence resonance energy transfer." Methods, 2001. 25(1): p. 78-86.

Hanna, M. et al., "Synthesis and characterization of a new photocrosslinking CTP analog and its use in photoaffinity labeling E. coli and T7 RNA polymerases", Nucleic Acids Res., 21(9):2073-2079 (1993).

Hansen, C.J , et al., "A robust and scalable microfluidic metering method that allows Protein crystal growth by free interface diffusion". Proc Natl Acad Sci U S A, 2002. 99 (26): p. 16531-6.

Harris, J.M., "Introducton to Biochemical and biomedical applications of poly(ethylene glycol)." poly(ethylene glycol) chemistry, Harris, J. M., Ed.; Plenum Press: New York, 1992: p. pp. 1-14.

Harrison et al., "Micromachining a miniaturized capillary electrophoresis-based chemical analysis system on a chip," Science, vol. 261, pp. 895-897 (1993).

Hasan, A. et al., "Photolabile Protecting Groups for Nucleosides: Synthesis and Photodeprotection Rates", Tetrahedron, 53(12):4247-4264 (1997).

Hornbeck, L. et al., "Bistable Defonnable Mirror Device", 1988 Techllical Digest Series, vol. 8, Optical Society of America, pp. 107-110, (Jun. 1988).

Hosokawa et al., "Handling of Picoliter liquid samples in a poly(dimethylsiloxane)-based microfluidic device," Anal. Chem., vol. 71, No. 20, pp. 4781-4785 (1999). http://biospace.intota.com (query "elastomer") cited by Examiner E Quan, GAU 1743 in related cases). http://www.chemfinder.com (cited by Examiner E. Quan, GAU 1743, in related case).

Houseal, T. et al., "Real-time imaging of single DNA molecules with fluorescence microscopy", Biophys. I., vol. 56, pp. 507-516 (Sep. 1989).

Hubner et al., "Direct observation of the triplet lifetime quenching of single dye molecules by molecular oxygen," J. Chem. Physics, 115, No. 21, Dec. 1, 2001, 9619-9622.

Hultman, T. et al., "Bidirectional Solid-Phase Sequencing ofIn Vitro-Amplified Plasmid DNA", BioTechniques, vol. 10, No. 1, pp. 84-93 (1991).

Hyman, E., "A New Method of Sequencing DNA", Anal. Biochem., 174:423-436 (1988).

Ishii et al., "Fluorescence resonance energy transfer between single fluorophores attached to a coiled-coil protein in aqueous solution," Chemical Physics, 247, 1999, 163-173.

Ishikawa, M. et al., "Single-Molecule Detection by Laser-Induced Fluorescence Technique with a Position-Sensitive Photon-Counting Apparatus", lpn. 1. Appl. Phys., vol. 33, Part 1, No. 3A, pp. 1571-1576 (1994).

Jacobs et al., "Combinatorial chemistry—applications oflight-directed chemical synthesis", TIBTech, vol. 12, pp. 19-26 (Jan. 1994).

Jacobson, K. et al., "International Workshop on the application of fluoresecence photobleaching techniques to problems in cell biology", Workshop Summary, Federation Proceedings, vol. 42, pp. 72-79 (1983).

Jacobson, et al., "High-speed separations on a microchip," Anal. Chem., vol. 66, No. 7, pp. 1114-1118 (1994).

Jacabson, et al., Microfluidic devices for electrokinetically driven parallel and serial mixing, Anal. Chem., vol. 71, No 20, pp. 4455-4459 (1999).

Jett, J. et al., "High-Speed DNA Sequencing: An Approach Based Upon Fluorescence Detection of Single Molecules", J. Biomolecular Structure & Dynamics, vol. 7, No. 2, pp. 301-309, (1989).

Johnston, R. et al., "Autoradiography using storage phosphor technology", Electrophoresis, 11 :355-360 (1990).

Jongeneel, C.V., et al., "Comprehensive sampling of gene expression in human cell lines with massively parallel signature sequencing". Proc Natl Acad Sci U S A, 2003.100(8): p. 636-639.

Joos, B. et al., "Covalent Attachment of Hybridizable Oligonucleotides to Glass Supports", Anal. Biochem. 247(1):96-101 (1997).

Kambara, H. et al., "Optimization of Parameters in a DNA Sequentor using Fluorescence Detection", Biotechnolof!Y, vol. 6, pp. 816-821 (1988).

Kartalov et al., "Single-Molecule Detection and DNA Sequencing-by-Synthesis," In Partial Fulfillment of the Requirements for the Degree of Doctor Philosophy, California Institute of technology, pp. 1-160 (2004).

Kartalov et al., "Poly-Electrolyte Surface-Chemistry Platform for Fluorescence Studies of DNA on Glass".

Kawai et al., "A simple method of detecting amplified DNA with immobilized probes on microtiter wells" 209, 63-69 (1993) Analytical Biochemistry.

Kelso et al.,v"Single-cell analysis by RT-PCR reveals differential expression of multiple type 1 and 2 cytokine genes among cells within polarized CD4+ T cell populations," International Immunology, 11, No. 4, 1999, 617-621.

Kenis et al., "Microfabrication inside capillaries using multiphase laminar flow patterning," Science, vol. 285, pp. 83-85 (1999).

Kenney, et al., "Mutation Typing Using Electrophoresis and Gel-Immobilized Acrydite™ Probes," BioTeechniques, vol. 25, No. 3, pp. 516-521, (1998).

Khandfian, E., "UV cross linking of RNA to nylon membrane enhances hybridization signals", Mole. Bio, Rep. 11: 107-115 (1986).

Khrapko, K. et al., "A method for DNA sequencing by hybridization with oligonucleotide matrix", DNA Sequence-J. DNA Sequencing and Mapping, vol. 1, pp. 375-388 (1991).

Kiefer, J. et al., "Crystal structure of a thermostable Bacillus DNA polymerase I large fragment at 2.1 A resolution", Structure, 5:95-108 (1997).

Kim, Y. et al., "Crystal structure of Thermus aquaticus DNA polymerase", Nature, 376:612-616 (1995).

Kirkland, T.A., D.M. Lynn, and R.H. Grubbs, "Ring-Closing Metathesis in Methanol and Water." Journal of Organic Chemistry, 1998.63(26): p. 9904-9909.

Knerr, L. and R.R. Schmidt, "Application of a ring-closing-metathesis-based linker to the solidphase synthesis of oligosaccharides" Synlett, 1999. 11: p. 1802-1804.

Kopp, et al., "Chemical Amplification: Continuous-Flow PCR on a Chip", Science, vol. 280, www.sciencemag.org., pp. 1046-1048 (May 1998).

Korolev, S. et al., "Crystal structure of the large fragment of Thermus aquaticus DNA polymerase I at 2.5 A resolution: Structural basis for thermo stability", PNAS, 92:9264-9268 (1995).

Kricka et al., "Labels, Labeling, Analytical Strategies, and Applications." Ch. 1 and Table Ix, Academic Press, New York (1995).

Krider, E. et al., "2'-Modified Nucleosides for Site-Specific Labeling of Oligonucleotides", Bioconjuf{. Chern., vol. 13, No. 1, pp. 155-162 (2002).

Kuhn, L. et al., "Silicon Charge Electrode Array for Ink Jet Printing", IEEE Trans. On Electron Dev., vol. ED-25, No. 10, pp. 1257-1260 (Oct. 1978).

Chidgeavadze et al., '2',3'-Dideoxy-3' aminonucleoside 5'-triphosphates are the terminators of DNA synthesis catalyzed by DNA polymerases, Nuc. Acids Res., 12(3):1671-1686 (1984).

Lacoste, T. et al., "Ultrahigh-resolution multicolor colocalization of single fluorescent ptobes", PNAS, 97(17):9461-6 (2000).

Lander, E.S., et al., "Initial sequencing and analysis of the human genome." Nature, 2001. 409(6822): p. 860-921.

Lazowski, K. et al., "Highly Sensitive Detection of Hybridization of OligonucleotideS to Specific Sequences of Nucleic Acids by Application of Fluorescence Resonance Energy Transfer", *Antisense and Nucleic Acid Dru Dev.*, vol. 10, pp. 97-103 (2000).

Lee, "Enhancing the catalytic repertoire of nucleic acids: a systematic study of linker length and rigidity," Nucleic Acids Res., 29, No. 7, Apr. 1, 2001, 1565-1573.

Lee, Y. et al., "Laser-Induced Fluorescence Detection of a Single Molecule in a Capillary", *Anal. Chern.*, vol. 66, pp. 4142-4149 (1994).

Levene, M. et al., "Zero-Mode Waveguides for Single-Molecule Analysis at High Concentrations", *Science*, 299:682-686 (Jan. 2003).

Levsky et al., "Single-cell expression profiling," Science, 297, Aug. 2, 2002, 836-840.

Li, H. et al., "Ultrasensitive Coincidence Fluorescence Detection of Single DNA Molecules", *Anal. Chern.*, 75:1664-1670 (2003).

Li, Y. et al., "Design, Synthesis, and Spectroscopic Properties of Peptide-Bridged Fluorescence Energy-Transfer Cassettes", *Bioconjuate Chern.*, 10:241-245 (1999).

Li, Y. et al., "Structural Studies of the Klentaq 1 DNA Polymerase", *Current Organic Chern.*, 5:871-883 (2001).

Li, Z. et al., "A photocleavable fluorescent nucleotide for DNA sequencing and analysis", *PNAS*, vol. 100, No. 2, pp. 414-419 (2003).

Lin, L. et al., "Free-Space Micromachined Optical Switches for Optical Networking", *IEEE J. of Selected Topics in Quanturn Electronics*, vol. 5, No. 1, pp. 4-9 (Jan. 1999).

Liu, J., M.. Enzelber, and S. Quake, "A nanoliter rotary device for polymerase chain reaction" Electrophoresis, 2002.23(10): p. 1531-6.

Lodder, M., et al., "Misacylated Transfer RNAs Having a Chemically Removable Protecting Group." Journal of Organic Chemistry, 1998.63(3): p. 794-803.

Loh, E. et al., "Polymerase Chain Reaction with Single-Sided Specificity: Analysis of T Cell Receptor D Chain", *Science* 243:217-220 (1989).

Lopez, G. et al., "Fabrication and Imaging of Two-Dimensional Patterns of Proteins Adsorbed on Self-Assembled Monolayers by Scanning Electron Microscopy", *J. Arner. Chern. Soc.*, 115:10774-81 (1993).

Lotters et al., "The mechanical properties of the rubber elastic polymer polydimethylsiloxane for sensor applications", J. Micromech. Microeng., vol. 7, pp. 145-147 (1997).

Lucy et al., "Characterization of the cationic surfactant induced reversal of electroosmotic flow in capillary electrophoresis," Anal. Chem., vol. 68, pp. 300-305 (1996).

Ludwig, J and F. Eckstein, "Rapid and efficient synthesis of nucleoside 5'-0-(lthiotriphosphates), 5'-triphosphates and 2',3'-cyclophosphorothioates using 2-chloro-4H-1,3,2benzodioxaphosphorin- 4-one." Journal of Organic Chemistry, 1989. 54(3): p. 631-635.

Maier, B., D. Bensimon, and V. Croquette, "Replication by a single DNA polymerase of a stretched single-stranded DNA." Proceedings of the National Academy of Sciences of the United States of America, 2000.97(22): p. 12002-12007.

Marriott, G. et al., "Time resolved imaging microscopy—Phosphorescence and delayed fluorescence imaging", *Biophys. J.*, vol. 60, pp. 1374-1387 (Dec. 1991).

Marziali, A. and M. Akeson, "New DNA sequencing methods." Annual Review of Biomedical Engineering, 2001. 3: p. 195-223.

Masterangelo., C. et al., "Vacuum-Sealed Silicon Micromachined Incandescent Light Source", *IDEM*, 89:503-506 (1989).

Meiners, J.C and S.R. Quake, "Femonewton force spectroscopy of single extended DNA. molecules." Phys Rev Lett, 2000. 84(21): p. 5014-7.

Meller, A., et al., "Rapid nanopore discrimination between single polynucleotide molecules." Proceedings of the National Academy of Sciences of the United States of America, 2000.97(3): p. 1079-1084.

Mertz, J. et al., "Single-molecule detection by two-photon-excited fluorescence", *Optics Letters*, vol. 20, No. 24, pp. 2532-2534 (Dec. 1995).

Metzker et al., "Elimination of residual natural nucleotides from 3'-O-modified-dNTP syntheses by enzymatic mop-up," BioTechniques, 25, Nov. 1998, 814-817.

Metzker, M.L., et al., "Termination of DNA synthesis by novel 3'-modified-deoxyribonucleoside 5'-triphosphates." Nucleic Acids Res, 1994.22(20): p. 4259-67.

Moe et al., Rapid Detection of Clinically Relevant Bacteria in Platelets Using the Hybriscan Bacetarial Detection system, Journal of the American Society of Hematology, 96, No. 11, 2000, 4155.

Muller et al., "Surface-micromachined microoptical elements and systems," IEEE vol. 86, No. 8, pp. 1705-1720 (1998).

Nelson, P. et al., "Bifunctional oligonucleotide probes synthesized using a novel CPG support are able to detect single base pair mutations", *NAR*, 17(18):7187-7194 (1989).

Nie, S. et al., "Probing Individual Molecules with Confocal Fluorescence Microscopy", *Science*, vol. 266, No. 5187, pp. 1018-1021 (Nov. 1994).

Nyren, P. et al., "Solid Phase DNA Minisequencing by an Enzymatic Luminometric Inorj:!;anic Pyrophosphate Detection Assay", *Anal. Biochem.*, vol. 208, pp. 171-175 (1993).

Ochman, H. et al., "Genetic Applications of an Inverse Polymerase Chain Reaction", *Genetics* 120:621-623 (1988).

Ohara, To et at, "'Wired' Enzyme Electrodes for Amperometric Determination of Glucose or Lactate in the Presence ofInterfering Substances",Ana/. *Chern.*, vol. 66, No. 15, pp. 2451-2457 (Aug.).

Ohara, T. et al., "Glucose Electrodes Based on Cross-Linked [Os(bpY)2CltH Complexed Poly(1-vinylimidazole) Films", *Ana/. Chem.*, vol. 65, pp. 3512-3517 (1993).

Okabe, S. et al., "Do Photobleached Fluorescent Microtubules Move?: Re-evaluation of Fluorescence Laser Photobleaching both In Vitro and in Growing Xenopus Axon", *J. Cell Bio/.*, vol. 120, No. 5, pp. 1177-1186 (1993).

Ollis, D. et al., Structure of large fragment of *E. coli* DNA polymerase I complexed with Dtmp, Nature, 313:762-766 (1985).

Oroskar, A. et al., "Detection of immobilized amplicons by ELISA-like techniques" *Clin. Chem.*, 42(9):1547-1555 (1996).

Patchornik, A. et al., "Photosensitive Protecting Groups" *J. Arner. Chern. Soc.*, 92(21):6333-37 (1970).

Padmaja, T., et al., "Enzymatically degradable prodrugs: a novel methodology for drug linkage." Journal of Applied Polymer Science, 2002.85(10): p. 2108-2118.

Pennisi, E., "Gene researchers hunt bargins, fixer-uppers." Science, 2002. 298(5594): p. 735-736.

Perales et al., "Enhancement of DNA, cDNA synthesis and fidelity at high temperatures by a dimeric single-stranded DNA-binding protein," Nucleic Acids Res., 31, No. 22, 2003, 6473-6480.

Perkins, T. et al., "Relaxation of a Single DNA Molecule Observed by Optical Microscopy", *Science*, 264:822-826 (May 1994).

Pethig, R. et at., "Applications of dielectrophoresis in biotechnology", *Tibtech*, vol. 15, pp. 426-432 (Oct. 1997).

Pisani, F. et at, "Domain Organization and DNA-Induced Conformational Changes of an Archaeal Family B DNA Polymerase", *Biochemistry*, vol. 35, pp. 9158-9166 (Jul. 1996).

Plakhotnik, T. et at, "Single-Molecule Spectroscopy", *Annu. Rev. Phys. Chem.*, vol. 48, pp. 181-212 (1997).

Ploem, J., Ch. 1 "Fluorescence Microscopy", Fluorescent and Luminescent Probes for BioL Activity, Mason, T. Ed., Academic Press, London, pp. 1-11 (1993).

Qin, P. et al., "Site-Specific Labeling ofRNA with Fluorophores and Other Structural Probes", *Methods*, vol. 18, No. 1, pp. 60-70 (May 1999).

Quake, S. et al., "Fluorescent Photobleaching Method for Sequencing DNA", pp. 1-10, circa 1996.

Quake, Stephen R. et al., "Methods and Apparatuses For Analyzing Polynucleotide Sequences", pending U.S. Appl. No. 09/707,737, filed Nov. 6, 2000.

Quake, S. et al., "Polymer Physics with Single Molecules of DNA" (Dept. of Physics), a colloquim by Stephen Quake, Stanford University, Feb. 22, 1996. (Presented at Laser Spectroscopy XII Intl. Conference, Italy, Jun. 1995.).

Quake, S. et al., "From Micro- to Nanofabrication with Soft Materials", *Science*, vol. 290, No. 5496, pp. 1536-1540 (Nov. 2000).

Guillier, F., D. Orain, and M. Bradley, "Linkers and Cleavage Strategies in Solid-Phase Organic Synthesis and Combinatorial Chemistry." Chemical Reviews, 2000. 100(6): p. 2091-2157.

Rapp, R. et al., "LIGA micropump for gases and liquids", *Sensors and Actuators A*, vol. 40, pp. 57-61 (1994).

Rigler, R., "Fluorescence correlations, single molecule detection and large number screening—Applications in Biotechnology", *J. Biotech.*, 41: 177-186 (1995).

Ronaghi, M. et al., "A Sequencing Method Based on Real-Time Pyrophosphate", *Science*, vol. 281, pp. 363-365 (Jul. 1998).

Rosenblum, B. et al., "New dye-labeled terminators for improved DNA sequencing patterns",*Nucleic Acids Research*, vol. 25, No. 22, pp. 4500-4504 (Nov. 1997).

Rosenblum, B. et al., "Improved single-strand DNA sizing accuracy in capillary electrophoresis", *Nucleic Acids Research*, vol. 25, No. 19, pp. 3925-3929 (Oct. 1997).

Roylance, L. et al., "A Batch-Fabricated Silicon Accelerometer", *IEEE Trans. On Elec. Dev.*, vol. ED-26, No. 12, pp. 1911-1917 (1979).

Ruth, J. et al., "Nucleoside Analogues with Clinical Potential in Antivirus Chemotherapy", *Molecular Pharmacology*, 20:415-422 (1981).

Sanger, F. et al., "DNA sequencing with chain-terminating inhibitors", *PNAS*, 74(12):5463-67 (Dec. 1977).

Sarfati, S.R., et al., "Synthesis of fluorescent derivatives of 3'-O-(6-aminohexanoyl)pyrimidine nucleosides 5'-triphosphztes that act as DNA polymerase substrates reversibly tagged at C-3'." Journal of the Chemical Society, Perkin Transactions I : Organic and Bio-Organic Chemistry, 1995.9: p. 1163-71.

Sato, E. et al., "Bimane Conjugates of 5-Halogenouridylic Acids as Fluorogenic Substrates for Phosphodiesterase I", *J. Chern. Research (S)*, Issue 10, pp. 390-391 (1994).

Sauer, M., et al.., "Single molecule DNA sequencing in submicrometer channels: state of the art and future prospects." Journal of Biotechnology, 2001. 86(3): p. 181.

Schasfoort et al., "Field-effect flow control for microfabricated fluidic networks," Science, vol. 286, pp. 942-945 (1999).

Seeger, S. et al., "Single molecule fluorescence—High Performance Molecular Diagnosis and Screening", translated from *BIOforum*, pp. 179-185, Apr. 1998.

Selvin, P., "Fluorescence Resonance Energy Transfer", Meth. In Enzymology, vol. 246, pp. 300-335, Academic Press (1995).

Shackelford, James F., "Intro. to Materials Science for Engineers." 3rd Edition, Prentice-Hall, Inc., Macmillan Publ. Co. (1992) (cited by Examiner E. Quan in related case).

Sharma, P., Gupta, K. etal., "A general method for the synthesis of3'-sulfhydryl and phosphate group containing oligonucleotides", *Nucleic Acids Res.*, 1901):3019-25 (1991).

Shendure et al., "Advanced sequencing technologies: Methods and goals," Nature, May 5, 2004, pp. 335-344.

Shoji, S. et al., "Smallest Dead Volume Microvalves for Integrated Chemical Analyzing Systems", *Proceedings of Transducers '91*, IEEE, pp. 1052-1055, San Francisco (1991).

Shoji, S. et al., "Fluids for Sensor Systems." Microsystem Technology in Chemistry and Life Science, Topics in Current Chem., vol. 194, pp. 162-188, Springer-Verlag (1998).

Smith, L. et al., "Fluorescence detection in automated DNA sequence analysis", *Nature*, vol. 321, pp. 674-679 (Jun. 1986).

Smith, L. et al., "The synthesis of oligonucleotides containing an aliphatic amino group at the 5' terminus: synthesis of fluorescent DNA primers for use in DNA sequence analysis", *Nucleic Acids Res.*, vol. 13, No. 7, pp. 2399-2412 (1985).

Smith, S. et al., "Direct Mechanical Measurements of the Elasticity of Single DNA Molecules by Using Magnetic Beads", *Science* 258:1122-26 (1992).

Smits, I., "Piezoelectric Micropump with Three Valves Working Peristaltically", *Sensors and Acutators*, vol. A21-A23, pp. 203-206 (1990).

Song et al., "Influence of the triplet excited state on the photobleaching kinetics of fluorescein in microscopy," Biophysics J., 70, Jun. 1996, 2959-2968.

Sproat, B. et al., "The synthesis of protected 5'-mercapto-2',5'-dideoxyribonucleoside- 3' -O-phosphoramidities; uses of 5'-mercapto-oligodeosyribonucleotides", *Nucleic Acids Res.*, 15(12):4837-48 (1987).

Strausberg, R L, et al., "The mammalian gene collection." Science, 1999.286(5439): p. 455-7.

Tasara et al., "Incorporation of reporter molecule-labeled nucleotides by DNA polymerases. II. High-density labeling of natural DNA," Nucleic Acids Res., 31, No. 10, 2003, 2636-2646.

Taveira, N. et al., "Detection HI VI proviral DNA by PCR and hybridization with digoxigenin labeled probes", *Mol. Cell Probes*, vol. 6, No. 4, pp. 265-270 (1992).

Taylor, D. et al., "Characterization of chemisorbed monolayers by surface potential measurements",J. *Phys. D. Appl. Phys.* 24:1443-50 (1991).

Terry, S. et al., "A Gas Chromatographic Air Analyzer Fabricated on a Silicon Wafer", *IEEE Trans. on Electron Dev.*, vol. ED-26, No. 12, pp. 1880-1886 (1979).

Theisen, P. et al., "Fluorescent dye phosphoramidite labeling of oligonucleotides", *Nucleic Acids Symp. Ser.*, vol. 27, pp. 99-100 (1992).

Thompson, N. et al., "Measuring Surface Dynamics of Biomolecules by Total Internal Reflection Fluorescence with Photobleaching Recovery or Correlation Spectroscopy", *Biophys. J.*, vol. 33, pp. 435-454 (Mar. 1981).

Thompson, N. et al., "Immunoglobulin Surface-Binding Kinetics Studied by Total Internal Reflection Fluorescence with Fluorescence Correlation Spectroscopy", *Biophys. J.*, vol. 43, pp. 103-114 (Jul. 1983).

Thorsen, T. S.J. Maerkl, and S.R. Quake, "Microfludic large-scale integration." Science, 202 298(5593): p. 580-4.

Tokunaga, M. et al., "Single Molecule Imaging of Fluorophores and Enzymatic Reactions Achieved by Objective-Type Total Internal Reflection Fluorescence Microscopy", *Biochem. And Biophys. Res. Comm.*, vol. 235, PD. 47-53 (1997).

Toneguzzo, F. et al., "Use of a Chemically Modified T7 DNA Polymerase for Manual and Automated Sequencing of Super coiled DNA", *BioTech*, vol. 6, No. 5, PD. 460-9 (1988).

Trager, R. S., "DNA sequencing—Venter's next goal: 1000 human genomes." Science, 2002. 298(5595): p. 947-947.

Tyagi, S. et al., "Multicolor molecular beacons for allele discrimination", *Nat. Biotechnol.*, 16:49-53 (1998).

Ullman's Encyclopedia of industrial Chemistry, 61D Edition, vol. 6, Sections 6 to 6.3, Subject: Carbon Black, Wiley-VCH (1999).

Unger et al., "Monolithic microfabricated valves and pumps by multilayer soft lithography," Science 288: 113-116 (2000).

Unger, M. et al., "Single-Molecule Fluorescence Observed with Mercury Lamp Illumination", *BioTechniques*, vol. 27, PD. 1008-1014 (Nov. 1999).

Vale, R. et al., "Direct observation of single kinesin molecules moving along microtubules", *Nature*, vol. 380, pp. 451-453, (Apr. 1996).

Van Dam, R.M. and S.R Quake, "Gene expression analysis with universal n-mer arrays." Genome Res, 2002. 12(1): p. 145-52.

Van De Pol, F. et al., "Micro-liquid handling devices: A Review", Micro System Technologies 90, 1st Intl. Conf. On Micro Electro, Opto, Mechanic Systems and Components, pp. 799-805, Berlin, Springer-Verlag, Sep. 1990.

Van Oijen et al., "Single molecule kinetics of λ exonuclease reveal base dependence and dynamic disorder," Science, 301, Aug. 29, 2003, 1235-1238.

Venter, J.L., et al., "The sequence of the human genome." Science, 2001. 291(5507): p. 1304-1351.

Vieider, C. et al., "A Pneumatically Actuated Micro Valve With A Silicone Rubber Membrane For Integration With Fluid-Handling Systems", *Proceedings of Transducers '95*, pp. 284-286, Stockholm (1995).

Walker, M.G., et al., "Prediction of gene function by genome-scale expression analysis: Prostate cancer-associated genes.": Genome Researce, 1999. 9(12): p. 1198-1203.

Wang, G. et al., "Design and Synthesis of New Fluorogenic HIV Protease Substrates Based on Resonance Energy Transfer", *Tetrahedron Lett.*, 31(45):6493-96 (1990).

Wang, M.D., et al., "Force and Velocity measured for single molecules of RNA polymerase." Science, 1998.282(5390): p. 902-907.

Washizu et al., "Molecular dielectrophoresis of biopolymers," IEEE Transactions on Industry Applications, vol. 30, No. 4, pp. 835-843 (1994).

Weber, J.L. and E.W. Myers, "Human whole-genome shotgun sequencing." Genome Research, 1997.7(5): p. 401-409.

Webster, J. et al., "Monolithic Capillary Gel Electrophoresis Stage with On-Chip Detector", Intl. Conf. on MEMS (MEMS 96), pp. 491-496 (1996).

Wedekind, P. et al., "Scanning microphotolysis: a new photobleaching technique based on fast intensity modulation of a scanned laser beam and confocal imaging", J. Microscopy, vol. 176, Pt. 1, pp. 23-33 (Oct. 1994).

Weir, et al., "Hybrigel Purification: A Novel Technique for Accelerated Prepration of DNA Sequence Products for Capillary Electrophoresis and Multiplexing," Clinical Chemistry, vol. 45, No. 11, p. 2052 (1999).

Weiss, S., "Fluorescence Spectroscopy of Single Biomolecules", Science, vol. 283, pp. 1676-1683 (Mar. 1999).

Welch, M.B. and K. Burgess, "Synthesis of fluorescent, photolabile 3'-O-protected nucleoside triphosphates for the base addition sequencing scheme." Nucleosides Nucleotides, 1999. 18(2): p. 197-201.

Williams, N. et al., "Exploring the Adenine Nucleotide Binding Sites on Mitochondrial FI-ATPase with a New Photoaffmity Probe, 3'-0-(4-Benzoyl)benzoyl Adenosine 5'-Triphosphate", J. Bioi. Chem., 237(6):2834-41 (1982).

Winter et al., "Direct gene expression analysis," Curr. Pharm. Biotech., 5, 2004, 191-197.

Wu, et al., "Synthesis and Properties of Adenosine-5'-triphosphoro-γ-l-(5-sulfonic acid)naphthyl Ethylamide: A Fluorescent Nucleotide Substrate for DNA-Dependent RNA Polymerase from Escherichia coli," Archives of Biochemistry and Biophysics, vol. 246, No. 2, pp. 564-571 (1986).

Wuite, G. et al., "Single-molecule studies of the. effect of template tension on T7 DNA polymerase activity", Nature, 404:103-6 (2000).

Xia et al., "Complex optical surfaces formed by replica molding against elastomeric masters," Science vol. 273, pp. 347-349 (1996).

Xia et al., "Soft Lithography," Angew. Chem. Int. Ed. vol. 37, pp. 550-575 (1998).

Xia, G., et al., "Directed evolution of novel polymerase activities: mutation of a DNA polymerase into a efficient RNA polymerase." Proc Natl Acad Sci USA; 2002. 99(10) p. 6597-602.

Xie, "Single molccule approach to dispersed kinetics and dynamic disorder: Probing conformational fluctuation and enzymatic dynamics," J. Chem. Physics, 117, No. 24, Dec. 22, 2002, 11024-11032.

Xu, X. et al., "Direct Measurement of Single-Molecule Diffusion and Photodecomposition in Free Solution", Science, vol. 275, pp. 1106-1109, (Feb. 1997).

Xu, X. et al., "Long-Range Electrostatic Trapping of Single-Protein Molecules at a Liquid-Solid Interface", Science, vol. 281, pp. 1650-1653 (Sep. 1998).

Yang et al., "A Mems Thermopneumatic Silicone Rubber Membrane Valve", Proceedings of IEEE 10th Annual International Workshop on MicroElectro Mechanical Systems, Sensors and Acuators, vol. A64, No. 1, pp. 101-108 (1998).

Yazdi, N. et al., "Micromachined Inertial Sensors", Proceedings of the IEEE, vol. 86, No., pp. 1640-1659 (Aug. 1998).

Yershov, G. et al., "DNA analysis and diagnostics on oligonucleotide microchips", Proc. Natl. Acad. Sci. USA, vol. 93, pp. 4913-4918 (May 1996).

Young et al., "Contoured elastic-membrane microvalves for microfluidic network integration," J. Biomechanical Engineering, vol. 121, pp. 2-6 (1999).

Yu., et al., "Cyanine dye dUTP analogs for enzymatic labeling of DNA probes." Nucleic Acids Res, 1994.22(15): p. 3226-32.

Zdeblick, M. et al., "A Microminiature Electric-To-Fluidic Valve", Transducers '87, reprinted in Micromechanics and MEMS Classic and Seminal Papers to 1990, IEEE Press, pp. 437-439 (1987).

Zhu, Z. et al., "Molecular Mechanism Controlling the Incorporation of Fluorescent Nucleotides into DNA by PCR", Cytometry, 28:206-211 (1997).

Zhu, Z. et al., "Directly labeled DNA probes using fluorescent nucleotides with different length linkers", Nucleic Acids Res., vol. 22, No. 16, pp. 3418-3422 (1994).

Zuckerman, R. et al., "Efficient methods for attachment of thiol specific probes to the 3' ends of synthetic oligodeoxyribonucleotides", Nucleic Acids Res., 15(13):5305-5321.

Ishijima, A. et al., "Simultaneous Observation of Individual ATPase and Mechanical Events by a Single Myosin Molecule during Interaction with Actin", Cell, vol. 92, pp. 161-171, (Jan. 1998).

Kovacs et al., "Simple synthesis of 5-vinyl-and 5-ethynyl-2' deoxyuridine 5'-triphosphates". Tetrahedron Letters, 1988. 29(36): p. 4525-8.

Korolev, S. et al., "Crystal structure of the large fragment of Thermus aquaticus DNA polymerase I at 2.5 A resolution: Structural basis for thermo stability", PNAS, 92:9264-9268 (1995).

Macklin, J. et al., "Imaging and Time-Resolved Spectroscopy of Single Molecules at an Interface", Science, vol. 272, No. 5259, pp. 255-258 (Apr. 1996).

Qin et al., "Elastomeric Light Valves," Advanced Materials vol. 9, No. 5, pp. 407-410 (1997).

Rasolonjatovo I. and S.R. Sarfati, "6-N-(N-methylanthranyamido)-4-oxo-hexanoic acid: a new florescent protecting group applicable to new DNA sequencing method." Nucleosides & Nucleotides, 1998.17(9-11): p. 2021-2025.

Rasolonjatovo, I. and Sarfati, "Development of a new DNA sequencing method: 3'-ester cleavage catalyzed by Taq DNA polymerase." Nucleosides & Nucleotides, 1999. 18(4 & 5): p. 1021-1022.

Rigler, R, et al, "DNA-sequencing at the single molecule level." Journal of Biotechnology, 2001. 86(3): p. 161.

Ronaghi, M et al., "Real-Time DNA Sequencing Using Detection of Pyrophosphate Release." Analytical BioChemistry, 242, No. 0432, 1996.

Tufte, O. et al., "Silicon Diffused-Element Piezoresistive Diaphragms", J. Applied Phys., vol. 31, No. 11, pp. 3322-3327 (Nov. 1962).

Watkins, R. et al., "A Total Internal-Reflection Technique for the Examination of Protein Adsorption", J. Bioned. Mater. Res., vol. 11, pp. 915-938 (1977).

Werner et al "Progress towards single-molecule DNA sequencing: a one color demonstration." J Biotechnol, 2003. 102(1): p. 1-14.

* cited by examiner

| Target Strand Analysis | |
|---|---|
| Length | Frequency |
| 1-mer | 5668 |
| 2-mer | 1394 |
| 3-mer | 333 |
| 4-mer | 94 |
| 5-mer | 27 |
| 6-mer | 3 |
| 7-mer | 1 |
| 8-mer | 0 |
| >=9-mer | 1 |

| Snythesized Strand Analysis | |
|---|---|
| Length | Frequency |
| 1-mer | |
| 2-mer | |
| 3-mer | |
| 4-mer | |
| 5-mer | |
| 6-mer | |
| 7-mer | |
| 8-mer | |
| >=9-mer | |

Inputs

Number of half-lives till dNTP's are flushed    0.8    0.9999307
*0.1-10.0 in increments of 0.1*

Number of wash cycles    60
*1-100 in increments of 1*

Number of strands to analyze (0-1000)    200

Number of strands with high homopolymer count (0-100)    0

Slowdown of second base incorporated in same wash    1
*Expressed as a multiple of slowdown (like 10X)*
*Base Case=1X; Poymerase Stall=1000X*

Outputs

| | | | |
|---|---|---|---|
| Longest extension in the ensemble of molecules | 50 | Bases | |
| Shortest extension in the ensemble of moleucles | 19 | Bases | |
| Average Extension | 32.76 | Bases | |
| Fraction of molecules which had 2 extensions in a homopolymer: | | | 77.0% |
| Fraction of molecules which had 3+ extensions in a homopolymer: | | | 4.5% |
| Fraction of molecules for which at least 25 bases sequenced: | | | 95.5% |

FIGURE 3

5 U/mL Klenow Fragment at 37°C
Cy3 analogs for all

SHORT CYCLE METHODS FOR SEQUENCING POLYNUCLEOTIDES

RELATED APPLICATIONS

This application claims the benefit of U.S. Provisional Application Nos. 60/546,277, filed on Feb. 19, 2004, 60/547,611, filed on Feb. 24, 2004, and 60/519,862, filed on Nov. 12, 2003.

FIELD OF THE INVENTION

The invention relates to methods for sequencing a polynucleotide, and more particularly, to methods for high throughput single molecule sequencing of target polynucleotides.

BACKGROUND

Completion of the human genome has paved the way for important insights into biologic structure and function. Knowledge of the human genome has given rise to inquiry into individual differences, as well as differences within an individual, as the basis for differences in biological function and dysfunction. For example, single nucleotide differences between individuals, called single nucleotide polymorphisms (SNPs), are responsible for dramatic phenotypic differences. Those differences can be outward expressions of phenotype or can involve the likelihood that an individual will get a specific disease or how that individual will respond to treatment. Moreover, subtle genomic changes have been shown to be responsible for the manifestation of genetic diseases, such as cancer. A true understanding of the complexities in either normal or abnormal function will require large amounts of specific sequence information.

An understanding of cancer also requires an understanding of genomic sequence complexity. Cancer is a disease that is rooted in heterogeneous genomic instability. Most cancers develop from a series of genomic changes, some subtle and some significant, that occur in a small subpopulation of cells. Knowledge of the sequence variations that lead to cancer will lead to an understanding of the etiology of the disease, as well as ways to treat and prevent it. An essential first step in understanding genomic complexity is the ability to perform high-resolution sequencing.

Various approaches to nucleic acid sequencing exist. One conventional way to do bulk sequencing is by chain termination and gel separation, essentially as described by Sanger et al., Proc Natl Acad Sci U S A, 74(12): 5463–67 (1977). That method relies on the generation of a mixed population of nucleic acid fragments representing terminations at each base in a sequence. The fragments are then run on an electrophoretic gel and the sequence is revealed by the order of fragments in the gel. Another conventional bulk sequencing method relies on chemical degradation of nucleic acid fragments. See, Maxam et al., Proc. Natl. Acad. Sci., 74: 560–564 (1977). Finally, methods have been developed based upon sequencing by hybridization. See, e.g., Drmanac, et al., Nature Biotech., 16: 54–58 (1998). Bulk techniques, such as those described above, cannot effectively detect single nucleotide differences between samples, and are not useful for comparative whole genome sequencing. Single molecule techniques are necessary for high-resolution detection of sequence differences.

There have been several recent reports of sequencing using single molecule techniques. Most conventional techniques have proposed incorporation of fluorescently-labeled nucleotides in a template-dependent manner. A fundamental problem with conventional single molecule techniques is that the sequencing reactions are run to completion. For purposes of single molecule chemistry, this typically means that template is exposed to nucleotides for incorporation for about 10 half lives. This gives rise to problems in the ability to resolve single nucleotides as they incorporate in the growing primer strand. The resolution problem becomes extreme in the situation in which the template comprises a homopolymer region. Such a region is a continuous sequence consisting of the same nucleotide species. When optical signaling is used as the detection means, conventional optics are able to reliably distinguish one from two identical bases, and sometimes two from three, but rarely more than three. Thus, single molecule sequencing using fluorescent labels in a homopolymer region typically results in a signal that does not allow accurate determination of the number of bases in the region.

One method that has been developed in order to address the homopolymer issue provides for the use of nucleotide analogues that have a modification at the 3' carbon of the sugar that reversibly blocks the hydroxyl group at that position. The added nucleotide is detected by virtue of a label that has been incorporated into the 3' blocking group. Following detection, the blocking group is cleaved, typically, by photochemical means to expose a free hydroxyl group that is available for base addition during the next cycle.

However, techniques utilizing 3' blocking are prone to errors and inefficiencies. For example, those methods require excessive reagents, including numerous primers complementary to at least a portion of the target nucleic acids and differentially-labeled nucleotide analogues. They also require additional steps, such as cleaving the blocking group and differentiating between the various nucleotide analogues incorporated into the primer. As such, those methods have only limited usefulness.

Need therefore exists for more effective and efficient methods and devices for single molecule nucleic acid sequencing.

SUMMARY OF THE INVENTION

The invention provides methods for high throughput single molecule sequencing. In particular, the invention provides methods for controlling at least one parameter of a nucleotide extension reaction in order to regulate the rate at which nucleotides are added to a primer. The invention provides several ways of controlling nucleic acid sequence-by-synthesis reactions in order to increase the resolution and reliability of single molecule sequencing. Methods of the invention solve the problems that imaging systems have in accurately resolving a sequence at the single-molecule level. In particular, methods of the invention solve the problem of determining the number of nucleotides in a homopolymer stretch.

Methods of the invention generally contemplate terminating sequence-by-synthesis reactions prior to completion in order to obtain increased resolution of individual nucleotides in a sequence. Fundamentally, this requires exposing nucleotides to a mixture comprising a template, a primer, and a polymerase under conditions sufficient for only limited primer extension. Reactions are conducted under conditions such that it is statistically unlikely that more than 1 or 2 nucleotides are added to a growing primer strand in any given incorporation cycle. An incorporation cycle comprises exposure of a template/primer to nucleotides directed at the base immediately downstream of the primer (this may be all four conventional nucleotides or analogs if the base is not known) and washing unhybridized nucleotide.

Nucleotide addition in a sequence-by-synthesis reaction is a stochastic process. As in any chemical reaction, nucleotide addition obeys the laws of probability. Methods of the invention are concerned with controlling the rate of nucleotide addition on a per-cycle basis. That is, the invention teaches ways to control the rate of nucleotide addition within an extension cycle given the stochastic nature of the extension reaction itself. Methods of the invention are intended to control reaction rates within the variance that is inherent in a reaction that is fundamentally stochastic. Thus, the ability to control, according to the invention, base addition reactions such that, on average, no more than two bases are added in any cycle takes into account the inherent statistics of the reactions.

The invention thus teaches polynucleotide sequence analysis using short cycle chemistry. One embodiment of the invention provides methods for slowing or reversibly inhibiting the activity of polymerase during a sequencing-by-synthesis reaction. Other methods teach altering the time of exposure of nucleotides to the template-primer complex. Still other methods teach the use of physical blockers that temporarily halt or slow polymerase activity and/or nucleotide addition. In general, any component of the reaction that permits regulation of the number of labeled nucleotides added to the primer per cycle, or the rate at which the nucleotides are incorporated and detected per cycle is useful in methods of the invention. Additional components include, but are not limited to, the presence or absence of a label on a nucleotide, the type of label and manner of attaching the label; the linker identity and length used to attach the label; the type of nucleotide (including, for example, whether such nucleotide is a dATP, dCTP, dTTP, dGTP or dUTP; a natural or non-natural nucleotide, a nucleotide analogue, or a modified nucleotide); the "half-life" of the extension cycle (where one half-life is the time taken for at least one incorporation to occur in 50% of the complementary strands); the local sequence immediately 3' to the addition position; whether such base is the first, second, third, etc. base added; the type of polymerase used; the particular batch characteristics of the polymerase; the processivity of the polymerase; the incorporation rate of the polymerase; the number of wash cycles (i.e., the number of times a nucleotide is introduced to the reaction then washed out); the number of target nucleic acids in the reaction; the temperature of the reaction and the reagents used in the reaction.

In a preferred embodiment of the invention, a nucleic acid template is exposed to a primer capable of hybridizing to the template and a polymerase capable of catalyzing nucleotide addition to the primer. A labeled nucleotide is introduced for a period of time that is statistically insufficient for incorporation of more than about 2 nucleotides per cycle. Nucleotide exposure may also be coordinated with polymerization inhibition such that, on average, 0, 1, or 2 labeled nucleotides are added to the primer, but that 3 labeled nucleotides are almost never added to the primer in each cycle. Ideally, the exposure time, during which labeled nucleotides are exposed to the template-primer complex, is statistically insufficient for incorporation of more nucleotides than are resolvable by a detection system used to detect incorporation.

The invention also contemplates performing a plurality of base incorporation cycles. Each cycle comprises exposing a template nucleic acid to a labeled nucleotide that is not a chain-terminating nucleotide. The labeled nucleotide is incorporated into a primer hybridized to the template nucleic acid if the nucleotide is capable of hybridizing to the template nucleotide immediately upstream of the primer and there is about a 99% probability that two or fewer of said nucleotides are incorporated into the same primer strand per cycle. Incorporated nucleotides are then identified.

Methods of the invention also make use of differential base incorporation rates in order to control overall reaction rates. For example, the rate of incorporation is lower for a second nucleotide given incorporation of a prior nucleotide immediately upstream of the second. This effect is magnified if the first nucleotide comprises a label or other group that hinders processivity of the polymerase. By determining an approximate reduction in the rate of incorporation of the second nucleotide, one can regulated the time of exposure of a sample to a second labeled nucleotide such that the time is statistically insufficient for incorporation of more nucleotides than are resolvable by a detection system used to detect incorporation of the nucleotide into the primer.

The invention may also be conducted using a plurality of primer extension cycles, wherein each cycle comprises exposing a target nucleic acid to a primer capable of hybridizing to the target, thereby forming a primed target; exposing the primed target to a labeled nucleic acid in the presence of a nucleic acid polymerase, coordinating transient inhibition of the polymerase and time of exposure to the labeled nucleotide such that it is statistically likely that at least one of said labeled nucleic acid is incorporated in the primer, but statistically unlikely that more than two of the labeled nucleotide are incorporated in the primer.

According to another embodiment, methods of the invention comprise conducting a cycle of template-dependent nucleic acid primer extension in the presence of a polymerase and a labeled nucleotide; inhibiting polymerase activity such that it is statistically unlikely that more than about 2 nucleotides are incorporated into the same primer strand in the cycle; washing unincorporated labeled nucleotide away from the template; detecting any incorporation of the labeled nucleotide; neutralizing label in any incorporated labeled nucleotide; removing the inhibition; repeating the foregoing steps; and compiling a sequence based upon the sequence of nucleotides incorporated into the primer.

In another embodiment, the invention provides a method comprising exposing a nucleic acid template to a primer capable of hybridizing to a portion of the template in order to form a template/primer complex reaction mixture; adding a labeled nucleotide in the presence of a polymerase to the mixture under conditions that promote incorporation of the nucleotide into the primer if the nucleotide is complementary to a nucleotide in the template that is downstream of said primer; coordinating removal of the labeled nucleotide and inhibition of the polymerase so that no more than about 2 nucleotides are incorporated into the same primer; identifying labeled nucleotide that has been incorporated into said primer; repeating the foregoing steps at least once; and determining a sequence of the template based upon the order of the nucleotides incorporated into the primer.

According to another embodiment, the method comprises exposing a template nucleic acid to a primer capable of hybridizing to a portion of the template upstream of a region of the template to be sequenced; introducing a labeled nucleic acid and a polymerase to the template under conditions wherein the labeled nucleic acid will be incorporated in the primer if the labeled nucleic acid is capable of hybridizing with a base downstream of the primer; and controlling the rate of the incorporation by limiting the time of exposure of the labeled nucleic acid to the template or by inhibiting the polymerase at a predefined time after exposure of the template to the labeled nucleotide; detecting incorporation of the labeled nucleotide into the primer; and identifying the nucleotide in the template as the complement of labeled nucleotide incorporated into the primer.

In yet another embodiment, methods of the invention comprise exposing a target polynucleotide to a primer capable of hybridizing to the polynucleotide, extending the primer in the presence of a polymerizing agent and one or more extendible nucleotides, each comprising a detectable label. The polymerizing agent is exposed to a cofactor (i.e., any agent that decreases or halts polymerase activity), and the incorporation of label is detected. The steps of extending the primer and exposing the polymerizing agent to a cofactor may be performed simultaneously, or may be performed in separate steps. In one embodiment, the method further comprises inactivating the cofactor, thereby reversing its effect on the polymerizing agent. Modes of inactivation depend on the cofactor. For example, where the cofactor is attached to the nucleotide, inactivation can typically be achieved by cleaving the cofactor from the nucleotide.

Methods of the invention also address the problem of reduced detection due to a failure of some strands in a given cycle to incorporate labeled nucleotide. In each incorporation cycle, a certain number of strands fail to incorporate a nucleotide that should be incorporated based upon its ability to hybridize to a nucleotide present in the template. The strands that fail to incorporate a nucleotide in a cycle will not be prepared to incorporate a nucleotide in the next cycle (unless it happens to be the same as the unincorporated nucleotide, in which case the strand will still lag behind unless both nucleotides are incorporated in the same cycle). Essentially, this situation results in the strands that failed to incorporate being unavailable for subsequent polymerase-catalyzed additions to the primer. That, in turn, leads to fewer strands available for base addition in each successive cycle (assuming the non-incorporation occurs in all or most cycles). The invention overcomes this problem by exposing a template/primer complex to a labeled nucleotide that is capable of hybridizing to the template nucleotide immediately downstream of the primer. After removing unbound labeled nucleotide, the sample is exposed to unlabeled nucleotide, preferably in excess, of the same species. The unlabeled nucleotide "fills in" the positions in which hybridization of the labeled nucleotide did not occur. That functions to increase the number of strands that are available for participation in the next round. The effect is to increase resolution in subsequent rounds over background. In a preferred embodiment, the labeled nucleotide comprises a label that impedes the ability of polymerase to add a downstream nucleotide, thus temporarily halting the synthesis reaction until unlabeled nucleotide can be added, at which point polymerase inhibition is removed and t he next incorporation cycle is conducted One feature of this embodiment is that a sequence is compiled based upon the incorporation data, while allowing maximum strand participation in each cycle. Thus, methods of the invention are useful for identifying placeholders in some strands in a population of strands being sequenced. As long as there are no more than two consecutive placeholders in any one strand, the invention has a high tolerance for placeholders with little or no effect on the ultimate sequence determination.

Methods of the invention are also useful for identifying a single nucleotide in a nucleic acid sequence. The method comprises the steps of sequentially exposing a template-bound primer to a labeled nucleotide and an unlabeled nucleotide of the same type in the presence of a polymerase under conditions that allow template-dependent primer extension; determining whether the first nucleotide is incorporated in the primer at a first position; repeating the sequentially exposing step using subsequent labeled and unlabeled nucleotides until a nucleotide is identified at the first position.

Identification of nucleotides in a sequence can be accomplished according to the invention using fluorescence resonance energy transfer (FRET). Single pair FRET (spFRET) is a good mechanism for increasing signal-to-noise in single molecule sequencing. Generally, a FRET donor (e.g., cyanine-3) is placed on the primer, on the polymerase, or on a previously incorporated nucleotide. The primer/template complex then is exposed to a nucleotide comprising a FRET acceptor (e.g., cyanine-5). If the nucleotide is incorporated, the acceptor is activated and emits detectable radiation, while the donor goes dark. That is the indication that a nucleotide has been incorporated. The nucleotide is identified based upon knowledge of which nucleotide species contained the acceptor. The invention also provides methods for identifying a placeholder in a nucleic acid sequence using FRET. A nucleic acid primer is hybridized to a target nucleic acid at a primer binding site in the target. The primer comprises a donor fluorophore. The hybridized primer is exposed to a first nucleotide comprising an acceptor fluorophore that, when incorporated into the primer, prevents further polymerization of the primer. Whether there is fluorescent emission from the donor and the acceptor is determined, and a placeholder in the nucleic acid sequence is identified as the absence of emission in both the donor and the acceptor.

In another embodiment, the method comprises hybridizing a nucleic acid primer comprising a donor fluorophore to a target nucleic acid at a primer binding site in the target; exposing the hybridized primer to a first nucleotide comprising an acceptor fluorophore that, when incorporated into the primer, prevents further polymerization of the primer; detecting the presence or absence of fluorescent emission from each of the donor and the acceptor; identifying a nucleotide that has been incorporated into the primer via complementary base pairing with the target as the presence of fluorescent emission from the acceptor; identifying a sequence placeholder as the absence of fluorescent emission from the donor and the acceptor; and repeating the exposing, detecting, and each of the identifying steps, thereby to compile a sequence of the target nucleic acid based upon the sequence of the incorporated nucleotides and the placeholders.

The invention is useful in sequencing any form of polynucleotides, such as double-stranded DNA, single-stranded DNA, single-stranded DNA hairpins, DNA/RNA hybrids, RNAs with a recognition site for binding of the polymerizing agent, and RNA hairpins. The invention is particularly useful in high throughput sequencing of single molecule polynucleotides in which a plurality of target polynucleotides are attached to a solid support in a spatial arrangement such that each polynucleotides is individually optically resolvable. According to the invention, each detected incorporated label represents a single polynucleotide.

A detailed description of the certain embodiments of the invention is provided below. Other embodiments of the invention are apparent upon review of the detailed description that follows.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2 are screenshots showing data from short cycle sequencing with long homopolymer regions.

FIG. 3 shows a short cycle embodiment for analyzing 200 target polynucleotides in a simulated synthesis of their complementary strands using short cycle periods of 0.8 half-life periods and repeating the wash cycles 60 times.

DETAILED DESCRIPTION

The invention provides methods for high throughput single molecule sequencing. According to the invention, one or more parameters of a sequencing-by-synthesis reaction are preselected such that the incorporation of, preferably, a single nucleotide on a primed target template is optically detectable. In one embodiment, the preselected parameters regulate the rate at which the nucleotides are incorporated, and the rate at which the incorporated nucleotides are detected. According to this embodiment, the nucleotides are individually detected either as they are incorporated or shortly thereafter, essentially in "real-time. In another embodiment, the preselected parameters permit the regulation of the number of nucleotides incorporated during a single extension cycle. In one aspect, the extension cycle is stopped short at a predetermined point at which, on average, only 0, 1, 2, or 3 nucleotides have been incorporated into the primer, rather than permitting the reaction to run to near or full completion in each cycle.

Short cycle methods according to the invention increase the resolution of individual nucleotides incorporated into the primer, but can decrease the yield of target templates successfully incorporating a nucleotide in a single extension cycle. In traditional full cycle sequencing, nucleotides may be allowed to react in the presence of a polymerizing agent until at least one becomes incorporated into at least 99% of the complementary strands. This would produce a yield of $(0.99)^n \times 100\%$ for a complementary strand extended by n nucleotides. Obtaining incorporation in 99% of the complementary strands, however, requires a period of several half-lives of the incorporation reaction, where one half-life is the time taken for at least one incorporation to occur in 50% of the complementary strands. Typically, the more strands that complete an incorporation during each cycle, the more n-mers obtained after n cycles.

Figure 1:
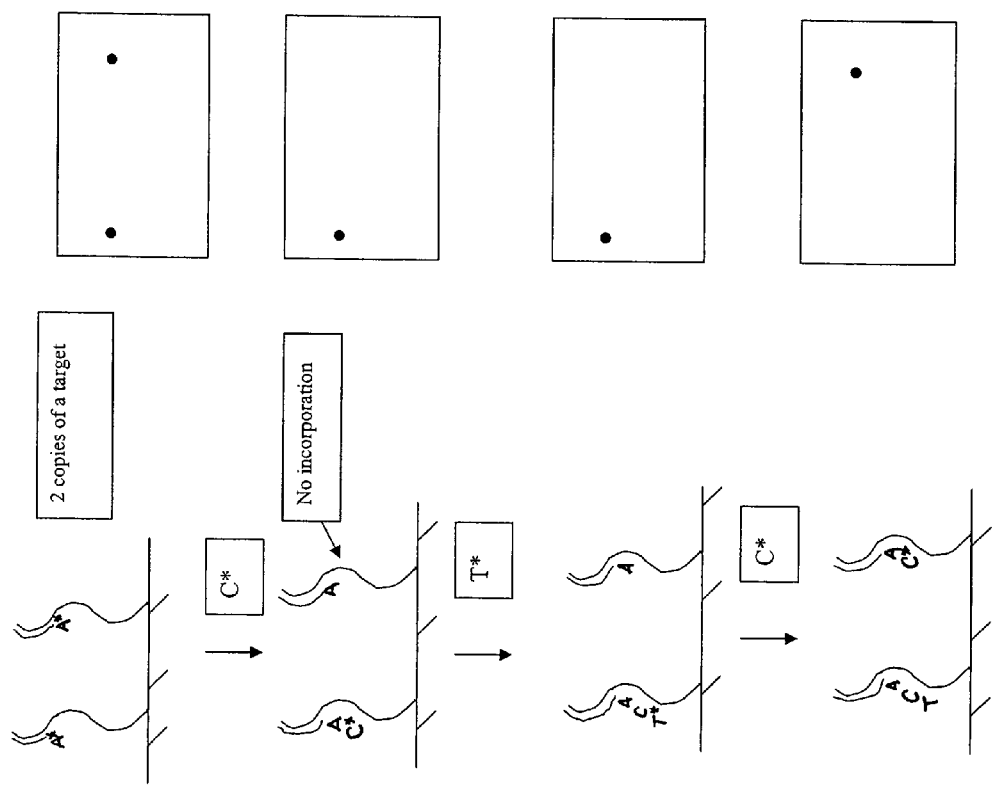
FIG. 1 shows asynchronous single molecule sequencing.

According to the invention, short cycle methods rely on a period of only a limited number of half-lives of exposure to nucleotides, thus resulting in fewer target templates having incorporated a nucleotide in the short extension cycle. However, the short sequencing cycles provided by methods of the invention allow asynchronous analysis of polynucleotides. Thus, if an incorporation reactions fails to occur on a particular target polynucleotide, it can be completed in a later cycle without producing erroneous information, or interfering with data from other target molecules being analyzed in parallel. As demonstrated in FIG. 1, a cytosine ("C") incorporates into the extension product of one copy of a target polynucleotide, but fails to incorporate into the other copy. During subsequent cycles of incorporation, however, a C can be incorporated, without adversely affection sequencing information. Thus, in asynchronous incorporation, an incorporation that failed to occur on a particular target in one-cycle can "catch up" in later cycles, permitting the use of shorter, even if more numerous, cycles.

Because short cycle methods according the invention permit the detection of, for example, one, two or three individual nucleotides incorporated into a primed template, the invention overcomes the difficulty posed by homopolymer regions of a template sequence. While detection techniques may be able to quantify signal intensity from a smaller number of incorporated nucleotides of the same base-type, for example two or three incorporated nucleotides, longer runs of identical bases may not permit quantification due to increasing signal intensity. That is, it may become difficult to distinguish n bases from n+1 bases, where the fractional increase in signal intensity from the (n+1)'h base is small relative to the signal intensity from the already-incorporated n bases.

In embodiments using short-cycles, it is possible to limit the number of nucleotides that become incorporated in a given cycle. For example, it can be determined by simulation that using a cycle period of about 0.8 half-lives can result in two or less incorporations in nine out of ten homopolymer complementary strands. (See Example 2b). In another simulation, a 0.8 half-life period was shown to allow no more than two incorporations in about 96.0% of 200 homopolymer complementary strands. As detection means can more readily quantify signal intensity from the smaller number of incorporated nucleotides rather than from larger numbers, the use of short-cycles addresses this issue. For example, imaging systems known in the art can reliably distinguish the difference in signal intensity between one versus two fluorescent labeling moieties on consecutively-incorporated nucleotides. Other imaging systems can reliably distinguish the difference in signal intensity between two versus three fluorescent labeling moieties on consecutively-incorporated nucleotides.

In a further embodiment of the invention, an extension cycle comprising a labeled nucleotide is followed by an extension cycle using an unlabeled nucleotide of the same type so that the position in each of the target template in which a labeled nucleotide failed to incorporated becomes occupied by an unlabeled nucleotide. Methods in accordance with this embodiment provide for continued participation of specific template nucleic acids in which no incorporation of the labeled nucleotide occurred and reduced probability of missing nucleotides in the resulting compiled sequence.

Further methods of the invention provide for identifying a placeholder in a nucleic acid sequence in the event that an accurate determination of a nucleotide at a particular position is not possible. A placeholder is simply a position of unknown identity. Such a placeholder may be represented in a nucleic acid sequence with, for example, an "X," a traditional symbol for an unspecified nucleotide. Slotting a placeholder in a nucleic acid sequence avoids frameshift-type errors in sequence determination.

Additional aspects of the invention are described in the following sections and illustrated by the Examples.

Target Nucleic Acids and Nucleotides

The invention is useful in sequencing any form of polynucleotides, including double-stranded DNA, single-stranded DNA, single-stranded DNA hairpins, DNA/RNA hybrids, RNAs with a recognition site for binding of the polymerizing agent, and RNA hairpins. Further, target polynucleotides may be a specific portion of a genome of a cell, such as an intron, regulatory region, allele, variant or mutation; the whole genome; or any portion therebetween. In other embodiments, the target polynucleotides may be mRNA, tRNA, rRNA, ribozymes, antisense RNA or RNAi. The target polynucleotide may be of any length, such as at least 10 bases, at least 25 bases, at least 50 bases, at least 100 bases, at least 500 bases, at least 1000 bases, or at least 2500 bases. The invention is particularly useful in high throughput sequencing of single molecule polynucleotides in which a plurality of target polynucleotides are attached to a solid support in a spatial arrangement such that each polynucleotides is individually optically resolvable. According to the invention, each detected incorporated label represents a single polynucleotide Nucleotides useful in the invention include both naturally-occurring and modified or non-naturally occurring nucleotides, and include nucleotide analogues. A nucleotide according to the invention may be, for example, a ribonucleotide, a deoxyribonucleotide, a modified ribonucleotide, a modified deoxyribonucleotide, a peptide nucleotide, a modified peptide nucleotide or a modified phosphate-sugar backbone nucleotide. Many aspects of nucleotides useful in the methods of the invention are subject to manipulation provide and suitable mechanisms for controlling the reaction. In particular, the species or type of nucleotide (i.e., natural or synthetic dATP, dCTP, dTTP, dGTP or dUTP; a natural or non-natural nucleotide) will affect the rate or efficiency of the reaction and therefore require consideration in preselecting parameters to produce the desire results.

In addition, certain modifications to the nucleotides, including attaching a label, will affect the reaction. The size, polarity, hydrophobicity, hydrophilicity, charge, and other chemical attributes should be considered in determining parameters that will produce the desired results in the reaction. Labeled nucleotides of the invention include any nucleotide that has been modified to include a label which is directly or indirectly detectable. Such labels include optically-detectable labels such fluorescent labels, including fluorescein, rhodamine, phosphor, polymethadine dye, fluorescent phosphoramidite, texas red, green fluorescent protein, acridine, cyanine, cyanine 5 dye, cyanine 3 dye, 5-(2'-aminoethyl)-aminonaphthalene-1-sulfonic acid (EDANS), BODIPY, ALEXA, or a derivative or modification of any of the foregoing. In one embodiment of the invention, fluorescence resonance energy transfer (FRET) technology is employed to produce a detectable, but quenchable, label. FRET may be used in the invention by, for example, modifying the primer to include a FRET donor moiety and using nucleotides labeled with a FRET acceptor moiety.

The fluorescently labeled nucleotides can be obtained commercially (e.g., from NEN DuPont, Amersham, and BDL). Alternatively, fluorescently labeled nucleotides can also be produced by various techniques, such as those described in Kambara et al., Bio/Techol. (1988) 6: 816–821; Smith et al., Nucl. Acid Res. (1985) 13: 2399–2412, and Smith et al., Nature (1986) 321: 674–79.

The fluorescent dye is preferably linked to the deoxyribose by a linker arm which is easily cleaved by chemical or enzymatic means. The length of the linker between the dye and the nucleotide can impact the incorporation rate and efficiency (see Zhu et al., Cytometry (1997) 28, 206). There are numerous linkers and methods for attaching labels to nucleotides, as shown in Oligonucleotides and Analogues: A Practical Approach (1991) (IRL Press, Oxford); Zuckerman et al., Polynucleotides Research (1987) 15: 5305–21; Sharma et al., Polynucleotides Research, (1991) 19: 3019; Giusti et al., PCR Methods and Applications (1993) 2: 223–227; Fung et al., U.S. Pat. No. 4,757,141; Stabinsky, U.S. Pat. No. 4, 739,044; Agrawal et al., Tetrahedron Letters, (1990) 31: 1543–46; Sproat et al., Polynucleotides Research (1987) 15: 4837; and Nelson et al., Polynucleotides Research, (1989) 17: 7187–94.

While the invention is exemplified herein with fluorescent labels, the invention is not so limited and can be practiced using nucleotides labeled with any form of detectable label, including radioactive labels, chemoluminescent labels, luminescent labels, phosphorescent labels, fluorescence polarization labels, and charge labels.

Reaction Parameters

Any parameter that permits the regulation of the number of labeled nucleotides added to the primer, or the rate at which the nucleotides are incorporated and detected can be controlled or exploited in the practice of the invention. Such parameters include, for example, the presence or absence of a label on a nucleotide, the type of label and manner of label attachment; the linker identity and length used to attach the label; the type of nucleotide (including, for example, whether such nucleotide is a dATP, dCTP, dTTP, dGTP or dUTP; a natural or non-natural nucleotide, a nucleotide analogue, or a modified nucleotide); the local sequence immediately 3' to the addition position; whether the base is the first, second, third, etc. base added; the type of polymerase used; the particular batch characteristics of the polymerase; the processivity of the polymerase; the incorporation rate of the polymerase, and use of polymerase cofactors.

In addition, a variety of the conditions of the reaction provide useful mechanisms for controlling either the number of nucleotides incorporated in a single extension reaction or the rates of nucleotide incorporation and detection. Such conditions include the "half-life" of the extension cycle (where one half-life is the time taken for at least one incorporation to occur in 50% of the complementary strands); the number of wash cycles (i.e., the number of times a nucleotide is introduced to the reaction then washed out); the number of target nucleic acids in the reaction; and the temperature of the reaction and the reagents used in the reaction.

Half-Lives and Wash Cycles

Based on the methods disclosed herein, those of skill in the art will be able to determine the period of half-lives required to limit the number incorporations per cycle for a given number of target polynucleotides. (See Examples 2 and 3, FIGS. 2 and 3). Statistical simulations can also provide the number of repeated cycles needed to obtain a given number of incorporations, for example, to sequence a 25 base pair sequence. (See Examples 2 and 3, FIGS. 2 and 3). Referring to the simulations above, for example, it can be determined that 60 cycles, each 0.8 half-lives long, would be required for at least 25 incorporations in each of ten complementary strands (Example 2b, FIG. 2b). With 200 complementary strands, 60 cycles each 0.8 half-lives long produce at least 20 incorporations in each strand (Example 3, FIG. 3). Following the methodologies outlined herein, such as the simulated working examples detailed below, those of skill in the art will be able to make similar determinations for other numbers of targets of varying lengths, and use appropriate cycle periods and numbers of cycles to analyze homopolymer without using blocking moieties or reversible chain termination.

The cycle period may also be chosen to permit a certain chance of incorporation of a given number of nucleotides in a complementary strand, and the cycle may be repeated a number of times to analyze the sequence of various numbers of target polynucleotides of varying length.

Figure 4:
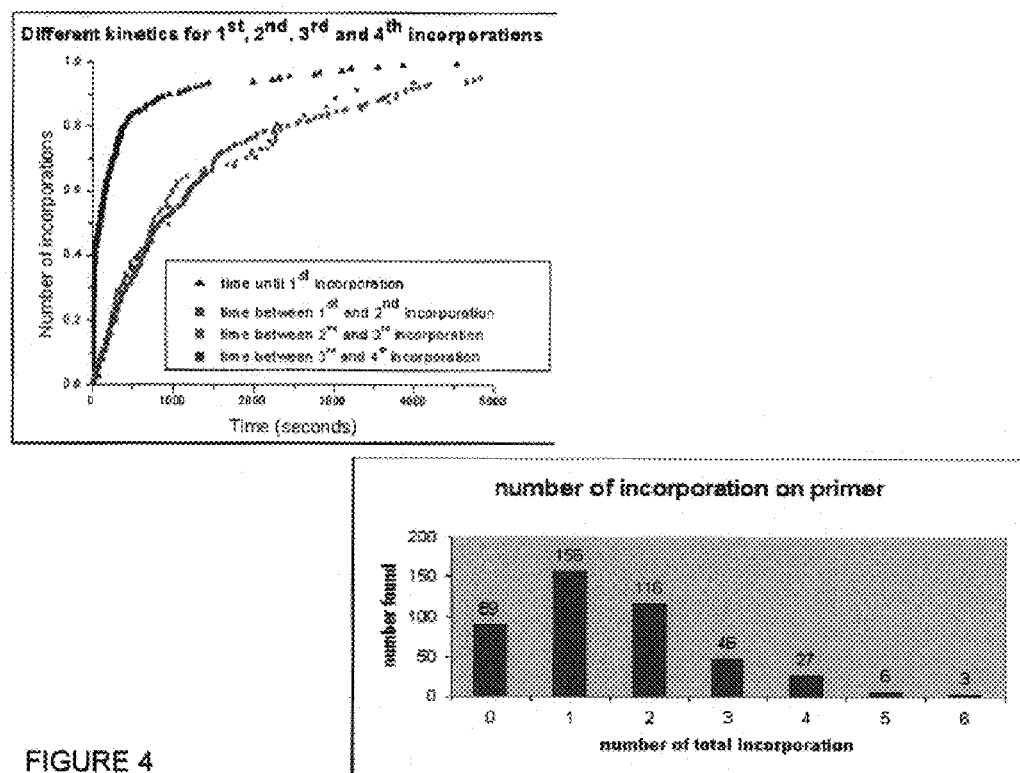
FIG. 4 shows a statistical analysis of incorporation, showing that polymerizing agent may incorporate repeat labeled nucleotides less readily than the first labeled nucleotide.

In some embodiments, nucleotide half-lives for the incorporation reaction are affected by the fact that polymerizing agent may incorporate labeled nucleotides less readily than unlabeled nucleotides. FIG. 4 illustrates the statistics of incorporation for a certain embodiment using a Klenow exo-minus polymerizing agent and Cy3- or Cy5-labeled nucleotides. The results show that polymerase may incorporate subsequent labeled nucleotides less readily than a prior labeled nucleotide. The graph of FIG. 4 indicates, for example, that it may take five to ten times longer, resulting in a "stalling" of the incorporation reaction. In other embodiments, the stalling may vary with the use of other labeled nucleotides, other polymerizing agents and various reaction conditions.

Polymerase stalling is a useful mechanism for controlling incorporation rates in single molecule reactions. As is shown in the Examples below, polymerase stalling is useful to limit incorporation of nucleotides into any given strand in a fairly precise manner. According to the invention, polymerase stalling is useful to limit incorporation to 1 nucleotide per strand per cycle, on average. Given a priori knowledge of the statistics of incorporation, single molecule reactions are controlled to provide a statistical likelihood that 1, sometimes 2, but rarely 3 nucleotides are incorporated in a strand in any given cycle.

For example, the rate at which polymerase incorporates labeled nucleotides into a complementary strand may be slowed by a factor of about 2, about 3, about 4, about 5, about 6, about 7, about 8, about 9, about 10, about 11, about 12, or about 15 times compared to that observed with unlabeled nucleotides or compared to that observed for a prior incorporated labeled nucleotide.

Figure 5:
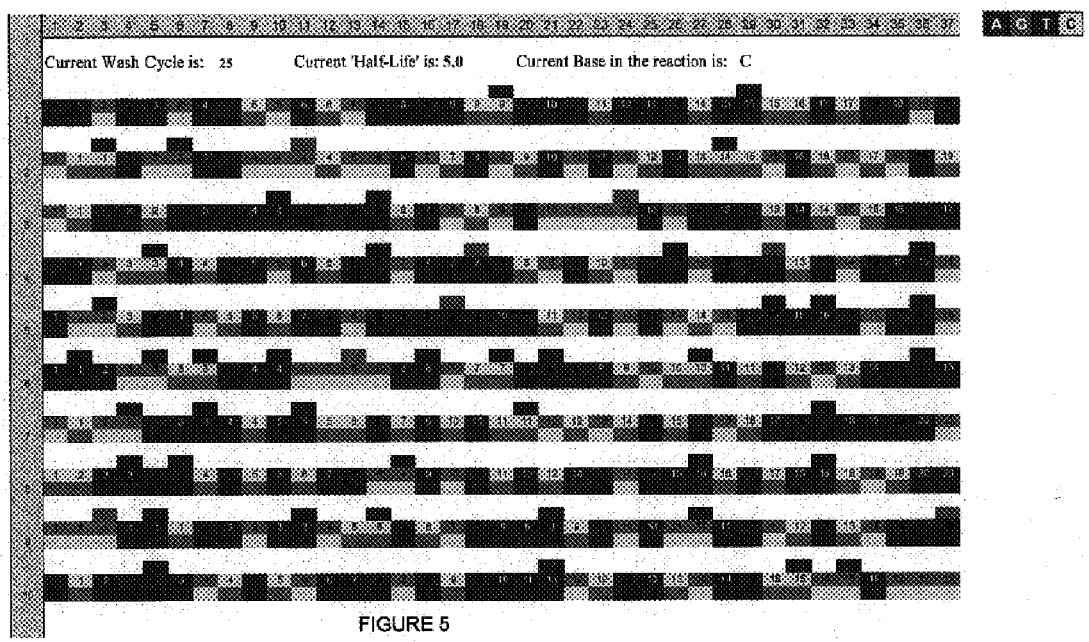
FIG. 5 shows a simulation showing the effect of decreasing the activity rate of the polymerizing agent and lengthening half-lives on the cycle period.
Figure 6:
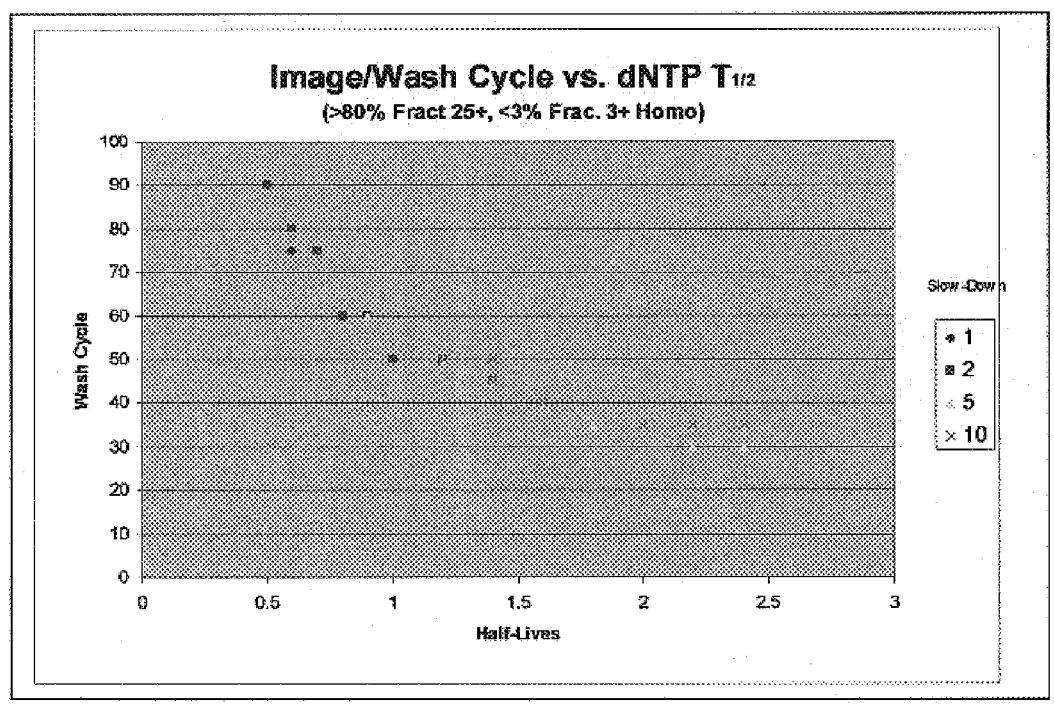
FIG. 6 shows the number of cycles needed with cycle periods of various half-lives taking into account stalling factors of two (squares), five (triangles) and 10 (crosses), in order to obtain over 25 incorporations in over 80% of target homopolymers, with at least a 97% chance of incorporating two or less nucleotides per cycle (or a smaller than 3% chance of incorporating more than 2 nucleotides per cycle).

Moreover, this inhibition or delaying and longer half-lives can be taken into account when determining appropriate cycle periods and numbers of cycles to analyze homopolymer targets of a given length. FIGS. 3 and 4, for example, illustrate the results of simulations in which various factors affecting incorporation rates are taken into account. The graph of FIG. 4, for example, shows the number of cycles needed with cycle periods of various half-lives, taking into account stalling factors of two (squares), five (triangles), and 10 (crosses), in order to obtain 25 incorporations in over 80% of target strands, with at least a 97% chance of incorporating two or fewer nucleotides per cycle (or a smaller than 3% chance of incorporating three or more nucleotides per cycle). As the graph shows, stalling allows longer half-lives, which, in turn, permits the use of fewer cycles to obtain a "full" sequence with a defined error rate. As FIG. 5 illustrates, if the use of labeled nucleotides slows down the polymerizing agent by a factor of 5, a cycle period of 2.4 half-lives produces over 80% 25-mers in 30 cycles. Based on the teachings of the invention, one of ordinary skill in the art can determine the cycle period required to limit the number incorporations per cycle for a given number of target polynucleotides of a given length.

Applying methods disclosed herein, the cycle period may be selected to permit about a 70%, about a 75%, about an 80%, about an 85%, about a 90%, about a 95%, about a 96%, about a 97%, about a 98%, and about a 99% chance of incorporation of two or less nucleotides into the complementary strand. Other cycle periods that may be used in embodiments of the invention include, for example, no more than about 5 half-lives, no more than about 4 half-lives, no more than about 3 half-lives, no more than about 2 half-lives, no more than about 1 half-lives, no more than about 0.9 half-lives, no more than about 0.8 half-lives, no more than about 0.7 half-lives, no more than about 0.6 half-lives, no more than about 0.5 half-lives, no more than about 0.4 half-lives, no more than about 0.3 half-lives, and no more than about 0.2 half-lives of the incorporation reactions.

In addition to the Examples provided below, various cycle periods and number of times the cycles are repeated may be used with various numbers of targets in certain embodiments of the invention. These include, for example, using about 200 target polynucleotides, a period of no more than about 0.6 half-lives and repeating at least about 50 times; using about 200 target polynucleotides, a period of no more than about 0.6 half-lives and repeating at least about 60 times; using about 200 target polynucleotides, a period of no more than about 0.6 half-lives and repeating at least about 70 times; using about 200 target polynucleotides, a period of no more than about 0.8 half-lives and repeating at least about 50 times; using about 200 target polynucleotides, a period of no more than about 0.8 half-lives and repeating at least about 60 times; using about 200 target polynucleotides, a period of no more than about 0.8 half-lives and repeating at least about 70 times; using about 200 target polynucleotides, a period of no more than about 1 half-life and repeating at least about 50 times; using about 200 target polynucleotides, a period of no more than about 1 half-life and repeating at least about 60 times; and using about 200 target polynucleotides, a period of no more than about 1 half-life and repeating at least about 70 times. In any of these embodiments, signal from incorporated nucleotides may be reduced after each or a number of cycles.

The number of times the cycles need to be repeated is also determined based on methods described herein. In general, the number of cycles increases with the length of the sequence to be analyzed and the duration of the half life of nucleotide exposure decreases as the length of sequence to be analyzed becomes longer. Also in general, half lives of nucleotide exposure increase and cycle numbers decrease with greater inhibitory or delaying effects on nucleotide incorporation Taking into account various stalling factors, examples of cycle periods and number repeat cycles that may be used in certain embodiments further include a cycle period of no more than about 0.5 half-lives with a stalling factor of about 2, repeated at least about 90 times; a cycle period of no more than about 0.75 half-lives, with a stalling factor of about 2, repeated at least about 75 times; a cycle period of no more than about 1 half-lives, with a stalling factor of about 2, repeated at least about 50 times; a cycle period of no more than about 1.5 half-lives with a stalling factor of about 2 or about 5, repeated at least about 45 times; a cycle period of no more than about 1.75 half-lives, with a stalling factor of about 5, repeated at least about 35 times; a cycle period of no more than about 2 half-lives, with a stalling factor of about 5 or about 10, repeated at least about 35 times; a cycle period of no more than about 2.25 half-lives, with a stalling factor of about 5 or about 10, repeated at least about 30 or at least about 35 times, and a cycle period of about 2.4 half-lives, with a stalling factor of about 5, repeated at least about 30 times.

Polymerases and Polymerase Cofactors

Polymerizing agents useful in the invention include DNA polymerases (such as Taq polymerase, T7 mutant DNA polymerase, Klenow and Sequenase, 9°N or a variant thereof), RNA polymerases, thermostable polymerases, thermodegradable polymerases, and reverse transcriptases. See e.g., Doublie et al., Nature (1998) 391:251–58; Ollis et al. Nature (1985) 313: 762–66; Beese et al., Science (1993) 260: 352–55; Korolev et al., Proc. Natl. Acad. Sci. USA (1995) 92: 9264–68; Keifer et al., Structure (1997) 5:95–108; and Kim et al., Nature (1995) 376:612–16.

Cofactors of the invention function to inhibit the polymerizing agent, thereby slowing or stopping synthesis activity, permitting the detection of an incorporated labeled nucleotide. Cofactors of the invention include any chemical agent or reaction condition that results in the inhibition of the polymerizing agent. Such inhibition may be in whole or in part and may be permanent, temporary or reversible. For example, a cofactor may be a label, an antibody, an aptamer, an organic or inorganic small molecule, or a polyanion, or it may comprise a chemical modification to a nucleotide (i.e., a nucleotide analogue may comprise a cofactor). A cofactor can be in solution, or it may be attached, either directly or through a linker to a nucleotide, primer, template or polymerase.

Examples of useful cofactor agents include, among others, light sensitive groups such as 6-nitoveratryloxycarbonyl (NVOC), 2-nitrobenzyloxycarbonyl (NBOC), α, α-dimethyl-dimethoxybenzyloxycarbonyl (DDZ), 5-bromo-7-nitroindolinyl, o-hyrdoxy-2-methyl cinnamoyl, 2-oxymethylene anthraquinone, and t-butyl oxycarbonyl (TBOC). Oligonucleotide Synthesis: A Practical Approach (IRL Press, Oxford). Useful polyanions are described in U.S. Pat. No. 6,667,165 (the disclosure of which is incorporated by reference herein); and useful aptamers are described in U.S. Pat. Nos. 6,020,130 and 6,183,967 (the disclosures of which are incorporated by reference herein). See U.S. Pat. No. 5,338,671 for useful antibodies. Nucleotides possessing various labels and cofactors can be readily synthesized. Labeling moieties are attached at appropriate sites on the nucleotide using chemistry and conditions as described in Gait (1984).

Further, the cofactor may also be the detectable label. Labels useful as combined labels/cofactors include larger or bulky dyes. For example, the detectable label may comprise a dye having a bulky chemical structure that, once the nucleotide is incorporated into the extending primer, causes a steric hindrance of the polymerizing agent, blocking the polymerizing agent from any further synthesis. Examples of labels that may be useful for this purpose are described in the Example, as well as in Zhu et al., Polynucleotides Res. (1994) 22: 3418–22. For example, fluorophore labels that may be used to stall the polymerase include Cy3, Cy5, Cy7, ALEXA647, ALEXA 488, BODIPY 576/589, BODIPY 650/665, BODIPY TR, Nile Blue, Sulfo-IRD700, NN382, R6G, Rho123, tetramethylrhodamine and Rhodamine X. In one embodiment, the labels are as bulky as Cy5, with molecular weights at least about 1.5 kDa. In another embodiment, the labels are bulkier than Cy5, having molecular weights of at least about 1.6 kDa, at least about 1.7 kDa, at least about 1.8 kDa, at least about 1.9 kDa, at least about 2.0 kDa at least bout 2.5 kDa, or at least about 3.0 kDa.

Further examples of such larger dyes include the following, with corresponding formula weights (in g/mol) in parentheses: Cy5 (534.6); Pyrene (535.6); 6-Carboxyfluorescein (FAM) (537.5); 6-Carboxyfluorescein-DMT (FAM-X (537.5); 5(6) Carboxyfluorescein (FAM) (537.5); 5-Fluorescein (FITC) (537.6); Cy3B (543.0); WellRED D4-PA (544.8); BODIPY 630/650 (545.5); 3' 6-Carboxyfluorescein (FAM) (569.5); Cy3.5 (576.7); Cascade Blue (580.0); ALEXA Fluor 430 (586.8); Lucifer Yellow (605.5); ALEXA Fluor 532 (608.8); WellRED D2-PA (611.0); Cy5.5 (634.8); DY-630 (634.8); DY-555 (636.2); WellRED D3-PA (645.0); Rhodamine Red-X (654.0); DY-730 (660.9); DY-782 (660.9); DY-550 (667.8); DY-610 (667.8); DY-700 (668.9); 6-Tetrachlorofluorescein (TET) (675.2) ALEXA Fluor 568 (676.8); DY-650 (686.9); 5(6)-Carboxyeosin (689.0); Texas Red-X (702.0); ALEXA Fluor 594 (704.9); DY-675 (706.9); DY-750 (713.0); DY-681 (736.9); Hexachlorofluorescein (HEX) (744.1); DY-633 (751.9); LightCycler Red 705 (753.0); LightCycler Red 640 (758.0); DY-636 (760.9); DY-701 (770.9); FAR-Fuchsia (5'-Amidite) (776.0); FAR-Fuchsia (SE) (776.0); DY-676 (808.0); Erythrosin (814); FAR-Blue (5'-Amidite) (824.0); FAR-Blue (SE) (824.0); Oyster 556 (850.0); Oyster 656 (900.0); FAR-Green Two (SE) (960.0); ALEXA Fluor 546 (964.4); FAR-Green One (SE), (976.0); ALEXA Fluor 660 (985.0); Oyster 645 (1000.0); ALEXA Fluor 680 (1035.0); ALEXA Fluor 633 (1085.0); ALEXA Fluor 555 (1135.0); ALEXA Fluor 647 (1185.0); ALEXA Fluor 750 (1185.0); ALEXA Fluor 700 (1285.0). These reagents are commercially available from SYNTHEGEN, LLC (Houston, Tex.).

There is extensive guidance in the literature for derivatizing fluorophore and quencher molecules for covalent attachment via common reactive groups that can be added to a nucleotide (see Haugland, Handbook of Fluorescent Probes and Research Chemicals (1992). There are also many linking moieties and methods for attaching fluorophore moieties to nucleotides, as described in Oligonucleotides and Analogues, supra; Guisti et al., supra; Agrawal et al, Tetrahedron Letters (1990) 31: 1543–46; and Sproat et al., Polynucleotide Research (1987) 15: 4837.

In one embodiment, the method further comprises inactivating the cofactor, thereby reversing its effect on the polymerizing agent. Modes of inactivation depend on the cofactor. For example, where the cofactor is attached to the nucleotide, inactivation can typically be achieved by chemical, enzymatic, photochemical or radiation cleavage of the cofactor from the nucleotide. Cleavage of the cofactor can be achieved if a detachable connection between the nucleotide and the cofactor is used. For example, the use of disulfide bonds enables one to disconnect the dye by applying a reducing agent like dithiothreitol (DTT). In a further alternative, where the cofactor is a fluorescent label, it is possible to neutralize the label by bleaching it with radiation.

In the event that temperature-sensitive cofactors are utilized, inactivation may comprise adjusting the reaction temperature. For example, an antibody that binds to thermostable polymerase at lower temperatures and blocks activity, but is denatured at higher temperatures, thus rendering the polymerase active; or single-stranded aptamers that bind to thermophilic polymerase at lower temperatures but are released at higher temperatures, may be inactivated by increasing the reaction temperature such the cofactor is released but polymerase activity is permitted.

In one embodiment, transient inhibition of the polymerase and the time of exposure to the labeled nucleotide are coordinated such that it is statistically likely that at least one of the labeled nucleotide is incorporated in the primer, but statistically unlikely that more than two of the labeled nucleotide are incorporated. In another embodiment, the reaction is controlled by inhibiting the polymerase activity such that it is statistically unlikely that more than, for example, one or two nucleotides are incorporated into the same primer strand in the cycle.

Temperature and Reagents

Other reaction conditions that are useful in the methods of the invention include reaction temperature and reagents. For example, a temperature above or below the temperature required for optimal activity of the polymerizing agent, such as a temperature of about 20–70°, would be expected to result in a modulation of the polymerization rate, C. This form of inhibition is typically reversible with correction of the reaction temperature, provided that the delta in temperature was insufficient to cause a permanent damage to the polymerase.

In another embodiment, buffer reagents useful in the methods of the invention include a detergent or surfactant, such as Triton®-X 100, or salt and/or ion concentrations that facilitate or inhibit nucleotide incorporation.

Predetermined Points for Stopping a Cycle

The predetermined point at which a short cycle is stopped is defined, for example, by the occurrence of an event (such as the incorporation of a nucleotide comprising a blocking moiety that prevents further extension of the primer), the lapse of a certain amount of time (such as a specific number of half-lives), or the achievement of a statistically-significant datapoint (such as a period at which a statistically significant probability of two or less nucleotides have been incorporated). In one embodiment, the predetermined period of time is coordinated with an amount of polymerization inhibition such that, on average, a certain number of labeled nucleotides are added to the primer. In another embodiment, the number of incorporated labeled nucleotides is, on average, 0, 1 or 2, but almost never more than 3. The time period of exposure is defined in terms of statistical significance. For example, the time period may be that which is statistically insufficient for incorporation of more nucleotides than are resolvable by a detection system used to detect incorporation of the nucleotide into the primer. In another example, the time period that is statistically insufficient for incorporation of a greater number of nucleotides that are individually optically resolvable during a predetermined detection period (i.e., a period of time during which the incorporated nucleotides are detected).

The reaction may be stopped by washing or flushing out the nucleotides that remain unincorporated and/or washing or flushing out polymerization agent. Further, many aspects of the repeated cycles may be automated, for example, using microfluidics for washing nucleotides to sites of anchored target polynucleotides, and washing out unincorporated nucleotides to halt each cycle.

The following exemplifications of the invention are useful in understanding certain aspects of the invention but are not intended to limit the scope of the invention in any way.

EXAMPLE 1

Primers are synthesized from nucleoside triphosphates by known automated oligonucleotide synthetic techniques, e.g., via standard phosphoramidite technology utilizing a nucleic acid synthesizer, such as the ABI3700 (Applied Biosystems, Foster City, Calif.). The oligonucleotides are prepared as duplexes with a complementary strand, however, only the 5' terminus of the oligonucleotide proper (and not its complement) is biotinylated.

Ligation of Oligonucleotides and Target Polynucleotides

Double stranded target nucleic acids are blunt-end ligated to the oligonucleotides in solution using, for example, T4 ligase. The single strand having a 5' biotinylated terminus of the oligonucleotide duplex permits the blunt-end ligation on only on end of the duplex. In a preferred embodiment, the solution-phase reaction is performed in the presence of an excess amount of oligonucleotide to prohibit the formation of concantamers and circular ligation products of the target nucleic acids. Upon ligation, a plurality of chimeric polynucleotide duplexes result. Chimeric polynucleotides are separated from unbound oligonucleotides based upon size and reduced to single strands by subjecting them to a temperature that destabilizes the hydrogen bonds.

Preparation of Solid Support

A solid support comprising reaction chambers having a fused silica surface is sonicated in 2% MICRO-90 soap (Cole-Parmer, Vernon Hills, Ill.) for 20 minutes and then cleaned by immersion in boiling RCA solution (6:4:1 high-purity $H_2O$/30% $NH_4OH$/30% $H_2O_2$) for 1 hour. It is then immersed alternately in polyallylamine (positively charged) and polyacrylic acid (negatively charged; both from Aldrich) at 2 mg/ml and pH 8 for 10 minutes each and washed intensively with distilled water in between. The slides are incubated with 5 mM biotin-amine reagent (Biotin-EZ-Link, Pierce) for 10 minutes in the presence of 1-[3-(dimethylamino)propyl]-3-ethylcarbodiimide hydrochloride (EDC, Sigma) in MES buffer, followed by incubation with Streptavidin Plus (Prozyme, San Leandro, Calif.) at 0.1 mg/ml for 15 minutes in Tris buffer. The biotinylated single-stranded chimeric polynucleotides are deposited via ink-jet printing onto the streptavidin-coated chamber surface at 10 pM for 10 minutes in Tris buffer that contain 100 mM $MgCl_2$.

Equipment

The experiments are performed on an upright microscope (BH-2, Olympus, Melville, N.Y.) equipped with total internal reflection (TIR) illumination, such as the BH-2 microscope from Olympus (Melville, N.Y.). Two laser beams, 635 (Coherent, Santa Clara, Calif.) and 532 nm (Brimrose, Baltimore), with nominal powers of 8 and 10 mW, respectively, are circularly polarized by quarter-wave plates and undergo TIR in a dove prism (Edmund Scientific, Barrington, N.J.). The prism is optically coupled to the fused silica bottom (Esco, Oak Ridge, N.J.) of the reaction chambers so that evanescent waves illuminated up to 150 nm above the surface of the fused silica. An objective (DPlanApo, 100 UV 1.3oil, Olympus) collects the fluorescence signal through the top plastic cover of the chamber, which is deflected by the objective to ≈40 μm from the silica surface. An image splitter (Optical Insights, Santa Fe, N.M.) directs the light through two bandpass filters (630dcxr, HQ585/80, HQ690/60; Chroma Technology, Brattleboro, Vt.) to an intensified charge-coupled device (I-PentaMAX; Roper Scientific, Trenton, N.J.), which records adjacent images of a 120-×60-µm section of the surface in two colors.

Experimental Protocols

FRET-Based Method Using Nucleotide-Based Donor Fluorophore

In a first experiment, universal primer is hybridized to a primer attachment site present in support-bound chimeric polynucleotides. Next, a series of incorporation reactions are conducted in which a first nucleotide comprising a cyanine-3 donor fluorophore is incorporated into the primer as the first extended nucleotide. If all the chimeric sequences are the same, then a minimum of one labeled nucleotide must be added as the initial FRET donor because the template nucleotide immediately 3' of the primer is the same on all chimeric polynucleotides. If different chimeric polynucleotides are used (i.e., the polynucleotide portion added to the bound oligonucleotides is different at least one location), then all four labeled dNTPs initially are cycled. The result is the addition of at least one donor fluorophore to each chimeric strand.

The number of initial incorporations containing the donor fluorophore is limited by either limiting the reaction time (i.e., the time of exposure to donor-labeled nucleotides), by polymerase stalling, or both in combination. The inventors have shown that base-addition reactions are regulated by controlling reaction conditions. For example, incorporations can be limited to 1 or 2 at a time by causing polymerase to stall after the addition of a first base. One way in which this is accomplished is by attaching a dye to the first added base that either chemically or sterically interferes with the efficiency of incorporation of a second base. A computer model was constructed using Visual Basic (v. 6.0, Microsoft Corp.) that replicates the stochastic addition of bases in template-dependent nucleic acid synthesis. The model utilizes several variables that are thought to be the most significant factors affecting the rate of base addition. The number of half-lives until dNTPs are flushed is a measure of the amount of time that a template-dependent system is exposed to dNTPs in solution. The more rapidly dNTPs are removed from the template, the lower will be the incorporation rate. The number of wash cycles does not affect incorporation in any given cycle, but affects the number bases ultimately added to the extending primer. The number of strands to be analyzed is a variable of significance when there is not an excess of dNTPs in the reaction. Finally, the inhibition rate is an approximation of the extent of base addition inhibition, usually due to polymerase stalling. The homopolymer count within any strand can be ignored for purposes of this application. FIG. 2 is a screenshot showing the inputs used in the model.

Figure 7A:
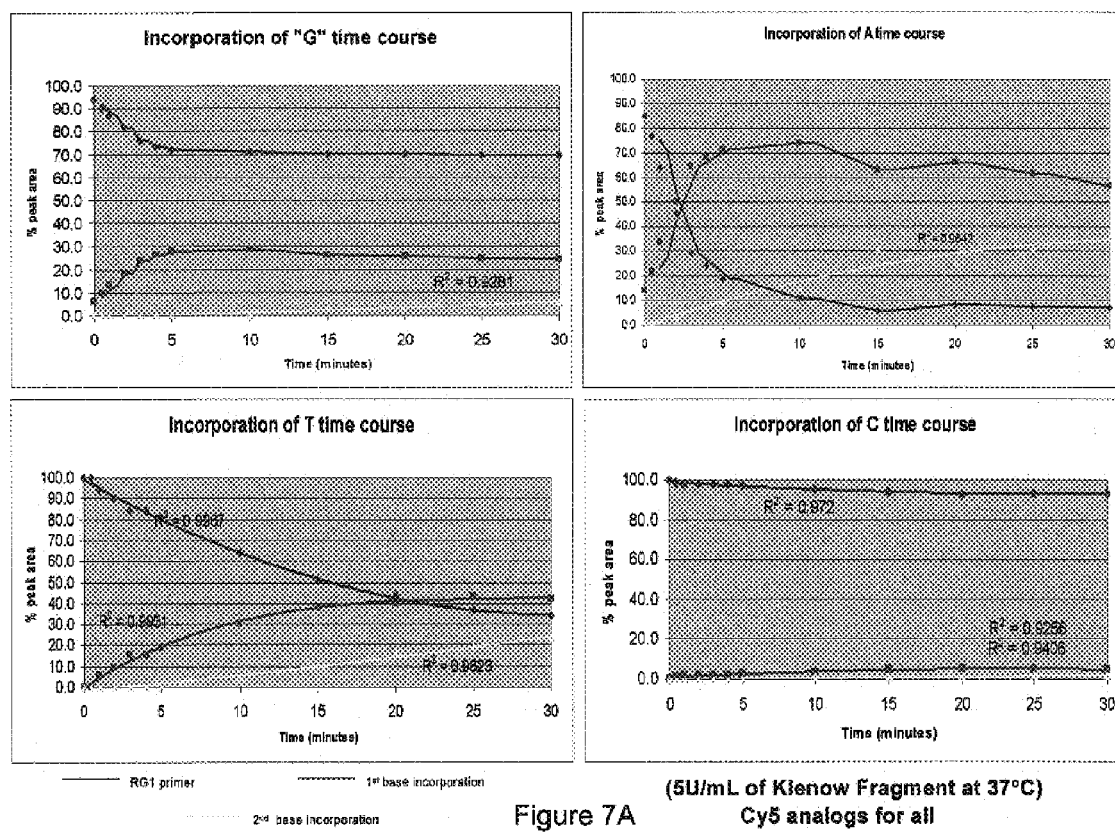
FIG. 7 is a series of screenshots showing the effects of altering reaction conditions on the incorporation of nucleotides in a single molecule sequencing by synthesis reaction.
Figure 7B:
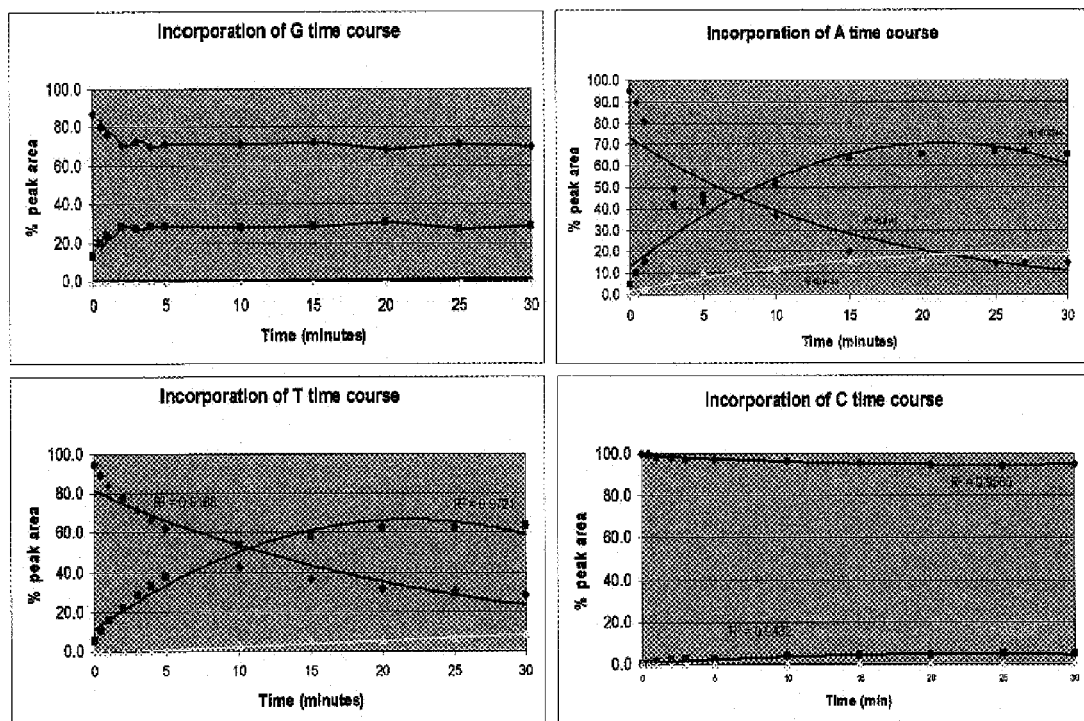

The model demonstrates that, by controlling reaction conditions, one can precisely control the number of bases that are added to an extending primer in any given cycle of incorporation. For example, as shown in FIG. 7, at a constant rate of inhibition of second base incorporation (i.e., the inhibitory effect of incorporation of a second base given the presence of a first base), the amount of time that dNTPs are exposed to template in the presence of polymerase determines the number of bases that are statistically likely to be incorporated in any given cycle (a cycle being defined as one round of exposure of template to dNTPs and washing of unbound dNTP from the reaction mixture). As shown in FIG. 7a, when time of exposure to dNTPs is limited, the statistical likelihood of incorporation of more than two bases is essentially zero, and the likelihood of incorporation of two bases in a row in the same cycle is very low. If the time of exposure is increased, the likelihood of incorporation of multiple bases in any given cycle is much higher. Thus, the model reflects biological reality. At a constant rate of polymerase inhibition (assuming that complete stalling is avoided), the time of exposure of a template to dNTPs for incorporation is a significant factor in determining the number of bases that will be incorporated in succession in any cycle. Similarly, if time of exposure is held constant, the amount of polymerase stalling will have a predominant effect on the number of successive bases that are incorporated in any given cycle (See, FIG. 7b). Thus, it is possible at any point in the sequencing process to add or renew donor fluorophore by simply limiting the statistical likelihood of incorporation of more than one base in a cycle in which the donor fluorophore is added.

Upon introduction of a donor fluorophore into the extending primer sequence, further nucleotides comprising acceptor fluorophores (here, cyanine-5) are added in a template-dependent manner. It is known that the Foster radius of Cy-3/Cy5 fluorophore pairs is about 5 nm (or about 15 nucleotides, on average). Thus, donor must be refreshed about every 15 bases. This is accomplished under the parameters outlined above. In general, each cycle preferably is regulated to allow incorporation of 1 or 2, but never 3 bases. So, refreshing the donor means simply the addition of all four possible nucleotides in a mixed-sequence population using the donor fluorophore instead of the acceptor fluorophore every approximately 15 bases (or cycles). FIG. 2 shows schematically the process of FRET-based, template-dependent nucleotide addition as described in this example.

The methods described above are alternatively conducted with the FRET donor attached to the polymerase molecule. In that embodiment, donor follows the extending primer as new nucleotides bearing acceptor fluorophores are added. Thus, there typically is no requirement to refresh the donor. In another embodiment, the same methods are carried out using a nucleotide binding protein (e.g., DNA binding protein) as the carrier of a donor fluorophore. In that embodiment, the DNA binding protein is spaced at intervals (e.g., about 5 nm or less) to allow FRET. Thus, there are many alternatives for using FRET to conduct single molecule sequencing using the devices and methods taught in the application. However, it is not required that FRET be used as the detection method. Rather, because of the intensities of the FRET signal with respect to background, FRET is an alternative for use when background radiation is relatively high.

Non-FRET Based Methods

Methods for detecting single molecule incorporation without FRET are also conducted. In this embodiment, incorporated nucleotides are detected by virtue of their optical emissions after sample washing. Primers are hybridized to the primer attachment site of bound chimeric polynucleotides Reactions are conducted in a solution comprising Klenow fragment Exo-minus polymerase (New England Biolabs) at 10 nM (100 units/ml) and a labeled nucleotide triphosphate in EcoPol reaction buffer (New England Biolabs). Sequencing reactions takes place in a stepwise fashion. First, 0.2 µM dUTP-Cy3 and polymerase are introduced to support-bound chimeric polynucleotides, incubated for 6 to 15 minutes, and washed out. Images of the surface are then analyzed for primer-incorporated U-Cy5. Typically, eight exposures of 0.5 seconds each are taken in each field of view in order to compensate for possible intermittency (e.g., blinking) in fluorophore emission. Software is employed to analyze the locations and intensities of fluorescence objects in the intensified charge-coupled device pictures. Fluorescent images acquired in the WinView32 interface (Roper Scientific, Princeton, N.J.) are analyzed using ImagePro Plus software (Media Cybernetics, Silver Springs, Md.). Essentially, the software is programmed to perform spot-finding in a predefined image field using user-defined size and intensity filters. The program then assigns grid coordinates to each identified spot, and normalizes the intensity of spot fluorescence with respect to background across multiple image frames. From those data, specific incorporated nucleotides are identified. Generally, the type of image analysis software employed to analyze fluorescent images is immaterial as long as it is capable of being programmed to discriminate a desired signal over background. The programming of commercial software packages for specific image analysis tasks is known to those of ordinary skill in the art. If U-Cy5 is not incorporated, the substrate is washed, and the process is repeated with dGTP-Cy5, dATP-Cy5, and dCTP-Cy5 until incorporation is observed. The label attached to any incorporated nucleotide is neutralized, and the process is repeated. To reduce bleaching of the fluorescence dyes, an oxygen scavenging system can be used during all green illumination periods, with the exception of the bleaching of the primer tag.

In order to determine a template sequence, the above protocol is performed sequentially in the presence of a single species of labeled dATP, dGTP, dCTP or dUTP. By so doing, a first sequence can be compiled that is based upon the sequential incorporation of the nucleotides into the extended primer. The first compiled sequence is representative of the complement of the template. As such, the sequence of the template can be easily determined by compiling a second sequence that is complementary to the first sequence. Because the sequence of the oligonucleotide is known, those nucleotides can be excluded from the second sequence to produce a resultant sequence that is representative of the target template.

EXAMPLE 2

Figure 2A:
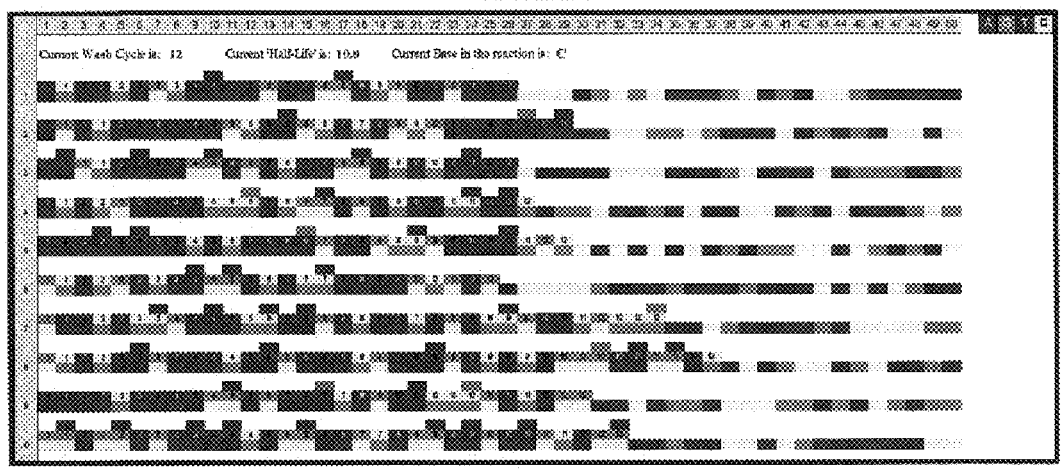
FIG. 2a shows full cycle sequencing used to analyze 10 target polynucleotides in a simulated synthesis of their complementary strands using cycle periods of 10 half-lives and repeating the wash cycles 12 times.
Figure 2B:
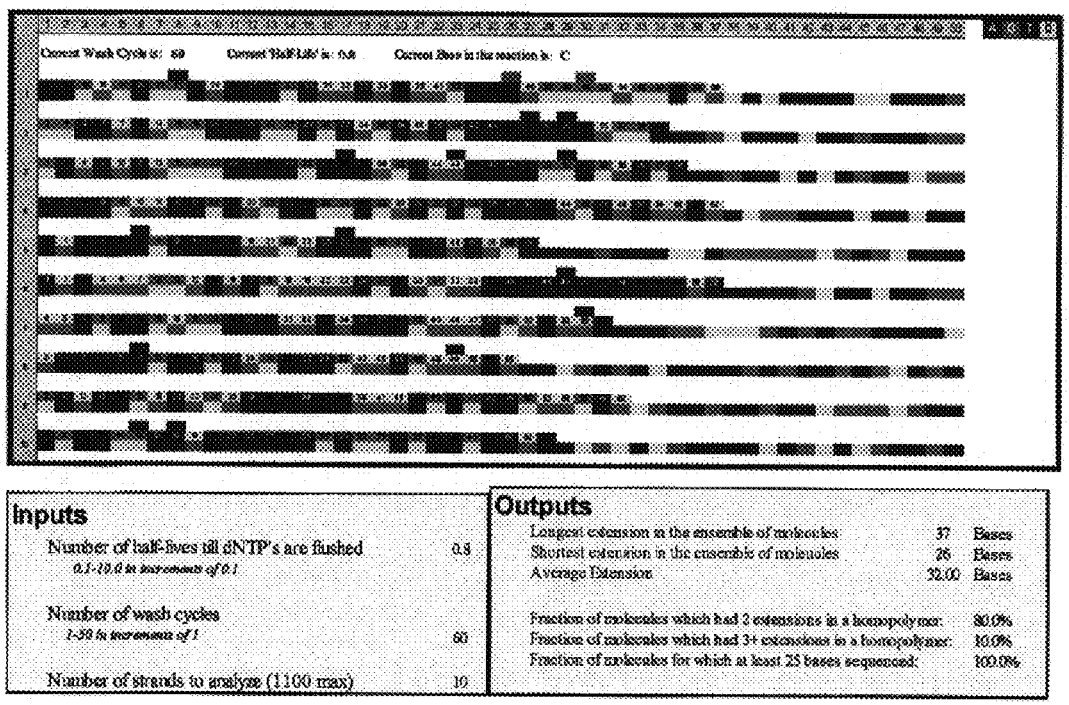
FIG. 2b shows a short cycle sequencing to analyze 10 target polynucleotides by simulating the synthesis of their complementary strands using short cycle periods of 0.8 half-life periods and repeating the wash cycles 60 times.

FIG. 2 illustrates the advantage of short-cycle sequencing with respect to avoiding long homopolymer reads. FIG. 2a illustrates a simulated analysis of 10 target polynucleotides using non-short-cycle sequencing (Example 2a), whereas FIG. 2b illustrates a simulated analysis of the same number of target polynucleotides using short-cycle sequencing (Example 2b).

The simulations were performed as follows: an Excel spreadsheet was opened and "Customize . . ." selected from the "Tools" menu of the Excel toolbar. The "Commands" tab was selected and, after scrolling down, "Macros" was clicked. The "smiley face" that appeared in the right panel was dragged to the toolbars on top of the spreadsheet. The "Customize" box was closed and the "smiley face" clicked once. From the list of subroutines that appeared, "ThisWorkbook.Main_Line." was selected. The program was run by clicking again on the "smiley face." A copy of the source code for the Excel simulation is provided below.

Input values were then entered into the tabbed sheet called "In Out." There were three input values:

The first input value corresponded to the period of time allowed for incorporation reactions of provided nucleotides into the growing complementary strands of the polynucleotides to be analyzed. This period was conveniently measured in half-lives of the incorporation reaction itself. Each cycle of incorporation was simulatedly stalled after a period of time, representing, for example, the time when unincorporated nucleotides would be flushed out or the incorporation reactions otherwise stalled.

The second input value corresponds to the number of times each cycle of incorporation was repeated. That is, the number of times the steps of providing nucleotides, allowing incorporation reactions into the complementary strands in the presence of polymerizing agent, and then stopping the incorporations are repeated. The nucleotides were simulatedly provided as a wash of each of dATPs, dGTPs, dTTPs, and dCTPs. The program then recorded which nucleotides were incorporated, corresponding to a detection step of detecting incorporation.

The third input value corresponds to number of strands of target polynucleotides to by analyzed in the simulation. The program allowed up to 1100 target polynucleotide molecules to be analyzed in a given simulation.

After the program was started, as described above, the program first generated the inputted number of strands composed of random sequences. The program then simulated hybridization and polymerization of the correct base of each incorporation reaction, based on the generated sequence of the target polynucleotide templates. The program continued these simulated reactions for the allowed amount of simulated time, determined by the inputted number of half-lives. Statistics of the simulation were then computed and reported, including the longest strand, the shortest strand, and the average length of all strands, as well as the fraction of strands extended by at least 25 nucleotide incorporations, as discussed in more detail below.

In the first part of this simulation, Example 2 a, the input values used were a cycle period of 10 half-lives, 12 repeats of the cycle, and 10 target polynucleotide strands.

FIG. 2a illustrates the results obtained. Homopolymers stretches which occurred in the same simulated complementary strand are highlighted in magenta wherever 2 nucleotides of the same base type were incorporated in a row, and in cyan wherever more than two nucleotides of the same base type were incorporated in a row.

FIG. 2a illustrates that the output values included the longest extended complementary strand obtained during the simulation (Longest extension in the ensemble of molecules); the shorted extended complementary strand obtained during the simulation (Shortest extension in the ensemble of molecules); and the average extension. These numbers represent the greatest number of incorporations into any of the 10 simulatedly growing complementary strands, the smallest number of incorporations for any of the 10, and the average number of incorporations for the 10.FIG. 2a indicates that the values obtained for Example 2a were 37 incorporations in the longest extension, 25 in the shortest, and 30.00 as the average number of incorporations.

The output values also provided information on the number of incorporations that occurred in each of growing complementary strands during each cycle period of the simulation. For example, FIG. 2a indicates that for the input values of Example 2a, the percentage of growing stands extended by two or more nucleotides in a homopolymer stretch was 100.0%; and the percentage of growing strands extended by three or more nucleotides in a homopolymer stretch was 60.0%. That is, using a cycle period of 10 half-lives resulted in only 40% of the complementary strands being extended by two or less nucleotides in a homopolymer stretch per cycle of incorporation.

Further, output values also indicated the total number of incorporations for each of the growing strands for the total number of repeated cycles. This represents the length of the sequence of target polynucleotide analyzed. FIG. 2a illustrates that in Example 2 a, 100.0% of the 10 target polynucleotides of the simulation were extended by at least 25 incorporated nucleotides. This illustrates that using a cycle period of 10 half-lives, and repeating the cycles 12 times, allowed analysis of a 25 base sequence of 10 target polynucleotides.

In the second part of this simulation, Example 2b, the input values used were a cycle period of 0.8 half-lives, 60 repeats of the cycle, and 10 target polynucleotide strands.

FIG. 2b illustrates the results obtained. Homopolymers stretches which occurred in the same simulated complementary strand are highlighted in magenta wherever 2 nucleotides of the same base type were incorporated in a row, and in cyan wherever more than two nucleotides of the same base type were incorporated in a row.

FIG. 2b illustrates that the output values included the longest extended complementary strand obtained during the simulation (longest extension in the ensemble of molecules); the shortest extended complementary strand obtained during the simulation (shortest extension in the ensemble of molecules); and the average extension. These numbers represent the greatest number of incorporations into any of the 10 simulatedly growing complementary strands, the smallest number of incorporations for any of the 10, and the average number of incorporations for the 10. FIG. 2b indicates that the values obtained for Example 2b were 37 incorporations in the longest extension, 26 in the shortest, and 32.00 as the average number of incorporations.

The output values also provided information on the number of incorporations that occurred in each of growing complementary strands during each cycle period of the simulation. For example, FIG. 2b indicates that for the input values of Example 2b, the percentage of growing stands extended by two or more nucleotides in a homopolymer stretch was 80.0%; and the percentage of growing strands extended by three or more nucleotides in a homopolymer stretch was 10.0%. That is, using a cycle period of 0.8 half-lives resulted in 90% of the complementary strands being extended by two or less nucleotides per cycle of incorporation.

Output values also indicated the total number of incorporations for each of the growing strands for the total number of repeated cycles. As in Example 2a, this represents the length of the sequence of target polynucleotide analyzed. FIG. 2b illustrates that in Example 2b, 100.0% of the 10 target polynucleotides of the simulation were again extended by at least 25 incorporated nucleotides. This illustrates that using a cycle period of 0.8 half-lives, and repeating the cycles 60 times, allowed analysis of a 25 base sequence of 10 target polynucleotides.

Comparing the two simulations, it will be appreciated by those in the art that the use of short-cycles of sequencing overcame issues of reading long repeats of homopolymer stretches in sequencing by synthesis, without using blocking moieties, as only a few nucleotides were incorporated per cycle. Comparing Examples 2a and 2b, the long cycles in 2a resulted in 40% of the extended complementary strands having two or less homopolymer nucleotide incorporations per cycle. Conversely, the short cycles in 11b resulted in 90% of the extended complementary strands having two or less homopolymer nucleotide incorporations per cycle, facilitating quantification. That is, as explained more thoroughly above, shorter reads can be quantitated to determine the number of nucleotides incorporated, for example, where the nucleotides are of the same Comparing Examples 2a and 2b also indicated that a greater number of repeated cycles were needed to analyze a given length of sequence when using shorter cycles. That is, the 10 half-lives cycle was repeated 12 times to result in 100.0% of the 10 complementary strands being extended by at least 25 nucleotides, whereas the 0.8 half-lives cycle was repeated 60 times to obtain this same result and thereby analyze the 25 nucleotides sequence.

Nonetheless, many aspects of the repeated cycles may be automated, for example, using micro fluidics for washing nucleotides to sites of anchored target polynucleotides, and washing out unincorporated nucleotides to halt each cycle.

As discussed herein, below is a copy of the source code for the simulation of short-cycle sequencing.

---

Source Code for Simulation of Short Cycle Sequencing

```
Option Explicit  'all variables must be declared
Option Base 1    'array pointers start at '1' not '0'
'-------Constant Declarations----------------------------------
Const NoColor = 0
Const Black = 1
Const White = 2
Const Red = 3
Const Green = 4
Const Blue = 5
Const Yellow = 6
Const Magenta = 7
Const Cyan = 8
Const A = Red
Const G = Green
Const T = Blue
Const C = Yellow
Const TENTH_HL = 0.93305
'-------Variable Declarations---------------------------------
'Note: HL is short for half-life
Dim MaxHalfLives As Integer 'The maximum number of half-lives the experiment will be run
X10 for each wash cycle
Dim HalfLives 'the Half Life variable is stepped in increments 0.1 half lives during every wash
cycle until the max is reached
```

-continued

Source Code for Simulation of Short Cycle Sequencing

```
Dim N, I, J, K, L, X, Y, Temp As Integer
Dim WashCyclesMax, WashCycles 'A wash cycle is completed after flowing each of AGT&C
Dim Molecule, Base, BaseType, Position As Integer
Dim TempReal As Single
Dim RandomMoleculesMax
Dim HomoPolymersMax
Dim MoleculesMax As Integer
'-----------the following three variables used to slow things down for second base
Dim Longer_HL As Single
Dim SecondMoleculeFactor As Integer
'------------The array variables----------
Dim TargetStrand(1100, 51) As Integer     '--up 1100 molecules, with max length of 50
Dim SynthesizedStrand(1100, 51) As Integer
Dim HL_Tracker(1100, 51) As Integer
Dim PolymerasePointer(1100) As Integer     '--contains the next available position on a given
strand
Dim StartPointer(1100) As Integer         'pointers for determining run-lengths
Dim StopPointer(1100) As Integer
Dim Extension(1100)                       'records how far each molecule has been extended
Dim TargetStrandFrequencyDist(15) As Integer   '--for storing frequency distribution of n-mers
of target strand
Dim SyntheticStrandFrequencyDist(15) As Integer '--for storing frequency distribution of n-mers
of target strand
Dim SecondMolecule(1100) As Boolean
'--------Code-----------------------------------------------
Sub Initialize( )
Dim XX As Integer
'-----clear the array which notes if a molecule is a second molecule
For Molecule = 1 To 1100
    SecondMolecule(Molecule) = False
Next Molecule
'Clear the arrays
For Base = 1 To 51
    For Molecule = 1 To 1100
        TargetStrand(Molecule, Base) = 0
        SynthesizedStrand(Molecule, Base) = 0
        HL_Tracker(Molecule, Base) = 0
        PolymerasePointer(Molecule) = 1
    Next Molecule
Next Base
For XX = 1 To 15   '--clear the frequency distribution list
    TargetStrandFrequencyDist(XX) = 0
    SyntheticStrandFrequencyDist(XX) = 0
Next XX
    For XX = 1 To 9
    Worksheets("In Out").Cells(5 + XX, 10).Value = ""
    Next XX
    With Worksheets("In Out")
        'Get the "front panel" input values
        TempReal = .Range("D4").Value
        MaxHalfLives = Int(TempReal * 10)
        WashCyclesMax = .Range("D7").Value
        RandomMoleculesMax = .Range("D9").Value
        If RandomMoleculesMax > 1000 Then RandomMoleculesMax = 1000
        HomoPolymersMax = .Range("D11").Value
        If HomoPolymersMax > 100 Then HomoPolymersMax = 100
        MoleculesMax = RandomMoleculesMax + HomoPolymersMax
        SecondMoleculeFactor = .Range("D14").Value
        Longer_HL = Exp(-0.0693 / SecondMoleculeFactor)
        '----Clear the output values
        .Range("D20").Value = ""
        .Range("D21").Value = ""
        .Range("D22").Value = ""
        .Range("E24").Value = ""
        .Range("E25").Value = ""
        .Range("E26").Value = ""
    End With
    'Worksheets("In Out").Range("E2").Value = Longer_HL   'Display the Longer_HL value
'Clear the output area & Fill Row headings
    With Worksheets("Molecules")
        .Range("B2:AY4006").ClearContents
        .Range("B2:AY4006").Interior.ColorIndex = NoColor
        For XX = 1 To 1100
            .Cells(3 + XX * 4, 1).Value = XX 'Add the row headings as running numbers
        Next XX
        .Range("B3").Value = "Current Wash Cycle is:"
        .Range("L3").Value = "Current 'Half-Life' is:"
```

Source Code for Simulation of Short Cycle Sequencing

```
            .Range("U3").Value = "Current Base in the reaction is:"
    End With
Randomize '---Seed the Random Number Generator
End Sub
Sub DrawSynthesizedStrands( )
Dim TempMolecule, TempBase As Integer
With Worksheets("molecules")
For TempBase = 1 To 50
    For TempMolecule = 1 To MoleculesMax
        If SynthesizedStrand(TempMolecule, TempBase) = Blue Then
            .Cells(TempMolecule * 4 + 2, TempBase + 1).Font.ColorIndex = 2
        Else
            .Cells(TempMolecule * 4 + 2, TempBase + 1).Font.ColorIndex = 0
        End If
        .Cells(TempMolecule * 4 + 2, TempBase + 1).Interior.ColorIndex =
SynthesizedStrand(TempMolecule, TempBase)
        If HL_Tracker(TempMolecule, TempBase) > 0 Then
            .Cells(TempMolecule * 4 + 2, TempBase + 1).Value = HL_Tracker(TempMolecule,
TempBase)
        End If
    Next TempMolecule
Next TempBase
End With
End Sub
Sub CreateTargetStrands( )
Dim TempRand As Integer
For Base = 1 To 50
    For Molecule = 1 To RandomMoleculesMax
        TempRand = Int(4 * Rnd + 3) 'random number of value 3,4,5 or 6
        'If TempRand = Blue Then TempRand = Cyan 'turn blue into cyan
        TargetStrand(Molecule, Base) = TempRand
        Worksheets("Molecules").Cells(Molecule * 4 + 3, Base + 1).Interior.ColorIndex =
TargetStrand(Molecule, Base)
    Next Molecule
Next Base
'--now draw molecules with long stretches of homopolymers
For Base = 1 To 50
    For Molecule = RandomMoleculesMax + 1 To MoleculesMax
        TargetStrand(Molecule, Base) = A
        Worksheets("Molecules").Cells(Molecule * 4 + 3, Base + 1).Interior.ColorIndex =
TargetStrand(Molecule, Base)
    Next Molecule
Next Base
End Sub
Sub Synthesize( )
Dim MoleculeSynthesized As Integer
Dim TempPointer As Integer
Dim Parameter As Single
For Molecule = 1 To 1100   'clear array which shows if molecule is a second molecule
    SecondMolecule(Molecule) = False
Next Molecule
For BaseType = A To C 'Cover each of AGT&C
    If BaseType = A Then Worksheets("Molecules").Range("AD3").Value = "A"
    If BaseType = G Then Worksheets("Molecules").Range("AD3").Value = "G"
    If BaseType = T Then Worksheets("Molecules").Range("AD3").Value = "T"
    If BaseType = C Then Worksheets("Molecules").Range("AD3").Value = "C"
    For HalfLives = 1 To MaxHalfLives
    Worksheets("Molecules").Range("R3").Value = HalfLives / 10
        For Molecule = 1 To MoleculesMax
            If SecondMolecule(Molecule) = False Then Parameter = TENTH_HL Else Parameter =
Longer_HL
            '-------------If we're flowing in A's, we attempt to polymerize only to T's
            If BaseType = A And TargetStrand(Molecule, PolymerasePointer(Molecule)) = T Then
                If Rnd > Parameter Then MoleculeSynthesized = 1 Else MoleculeSynthesized = 0 'did
molecule go?
                If MoleculeSynthesized = 1 Then
                    SecondMolecule(Molecule) = True
                    SynthesizedStrand(Molecule, PolymerasePointer(Molecule)) = A
                    HL_Tracker(Molecule, PolymerasePointer(Molecule)) = WashCycles
                    PolymerasePointer(Molecule) = PolymerasePointer(Molecule) + 1
                    If PolymerasePointer(Molecule) > 50 Then PolymerasePointer(Molecule) = 50
                End If
            End If
            '-------------If we're flowing in T's, we attempt to polymerize only to A's
            If BaseType = T And TargetStrand(Molecule, PolymerasePointer(Molecule)) = A Then
                If Rnd > Parameter Then MoleculeSynthesized = 1 Else MoleculeSynthesized = 0 'did
molecule go?
```

Source Code for Simulation of Short Cycle Sequencing

```
                        If MoleculeSynthesized = 1 Then
                            SecondMolecule(Molecule) = True
                            SynthesizedStrand(Molecule, PolymerasePointer(Molecule)) = T
                            HL_Tracker(Molecule, PolymerasePointer(Molecule)) = WashCycles
                            PolymerasePointer(Molecule) = PolymerasePointer(Molecule) + 1
                            If PolymerasePointer(Molecule) > 50 Then PolymerasePointer(Molecule) = 50
                        End If
                    End If
                '-------------If we're flowing in G's, we attempt to polymerize only to C's
                    If BaseType = G And TargetStrand(Molecule, PolymerasePointer(Molecule)) = C Then
                        If Rnd > Parameter Then MoleculeSynthesized = 1 Else MoleculeSynthesized = 0 'did
molecule go?
                        If MoleculeSynthesized = 1 Then
                            SecondMolecule(Molecule) = True
                            SynthesizedStrand(Molecule, PolymerasePointer(Molecule)) = G
                            HL_Tracker(Molecule, PolymerasePointer(Molecule)) = WashCycles
                            PolymerasePointer(Molecule) = PolymerasePointer(Molecule) + 1
                            If PolymerasePointer(Molecule) > 50 Then PolymerasePointer(Molecule) = 50
                        End If
                    End If
                '-------------If we're flowing in C's, we attempt to polymerize only to G's
                    If BaseType = C And TargetStrand(Molecule, PolymerasePointer(Molecule)) = G Then
                        If Rnd > Parameter Then MoleculeSynthesized = 1 Else MoleculeSynthesized = 0 'did
molecule go?
                        If MoleculeSynthesized = 1 Then
                            SecondMolecule(Molecule) = True
                            SynthesizedStrand(Molecule, PolymerasePointer(Molecule)) = C
                            HL_Tracker(Molecule, PolymerasePointer(Molecule)) = WashCycles
                            PolymerasePointer(Molecule) = PolymerasePointer(Molecule) + 1
                            If PolymerasePointer(Molecule) > 50 Then PolymerasePointer(Molecule) = 50
                        End If
                    End If
                Next Molecule
                'DrawSynthesizedStrands '--for now, display is refreshed after each increment of half life
for a given base
            Next HalfLives
    Next BaseType
End Sub
'---Develop an analysis of the distribution of homopolymers in the full-length targets, report as a
frequency
'---distribution of n-mers
Sub AnalyzeTargetStrands( )
Dim CurrentBase As Integer
Dim BasesAhead As Integer
Dim N As Integer
Dim NumberedBases(50) As Integer
Dim RunLengths(50) As Integer
For N = 1 To 15   '--clear the frequency distribution list
    TargetStrandFrequencyDist(N) = 0
    SyntheticStrandFrequencyDist(N) = 0
Next N
For Molecule = 1 To MoleculesMax 'Identify Changes among bases
    NumberedBases(1) = 1
    'Worksheets("Molecules").Cells(4 + Molecule * 4, 2).Value = NumberedBases(1) 'take this
out. For display only
        For Base = 2 To 50
            If TargetStrand(Molecule, Base - 1) < > TargetStrand(Molecule, Base) Then
                NumberedBases(Base) = 1
            Else
                NumberedBases(Base) = 0
            End If
            'Worksheets("Molecules").Cells(4 + Molecule * 4, Base + 1).Value =
NumberedBases(Base) 'take this out. For display only
        Next Base
    '---------------compute run lengths
    '''''But first we've got a boundary condition problem for the first base--we solve it here!!
    RunLengths(1) = 1
    'Worksheets("Molecules").Cells(5 + Molecule * 4, 2).Value = RunLengths(1)
    For Base = 2 To 50
        If NumberedBases(Base) = 1 Then
            RunLengths(Base) = 1
        Else
            RunLengths(Base) = RunLengths(Base - 1) + 1
        End If
        'Worksheets("Molecules").Cells(5 + Molecule * 4, Base + 1).Value = RunLengths(Base)
    Next Base
    '----save only the terminal value of a run length
```

-continued

Source Code for Simulation of Short Cycle Sequencing

```
      For Base = 1 To 49
          If RunLengths(Base + 1) > RunLengths(Base) Then RunLengths(Base) = 0
          'Worksheets("Molecules").Cells(6 + Molecule * 4, Base + 1).Value = RunLengths(Base)
      Next Base
      'Worksheets("Molecules").Cells(6 + Molecule * 4, 50 + 1).Value = RunLengths(50)
'boundary condition
      '-----Now determine the frequency distribution of each N-mer
      For Base = 1 To 50
          If RunLengths(Base) = 1 Then TargetStrandFrequencyDist(1) =
TargetStrandFrequencyDist(1) + 1
          If RunLengths(Base) = 2 Then TargetStrandFrequencyDist(2) =
TargetStrandFrequencyDist(2) + 1
          If RunLengths(Base) = 3 Then TargetStrandFrequencyDist(3) =
TargetStrandFrequencyDist(3) + 1
          If RunLengths(Base) = 4 Then TargetStrandFrequencyDist(4) =
TargetStrandFrequencyDist(4) + 1
          If RunLengths(Base) = 5 Then TargetStrandFrequencyDist(5) =
TargetStrandFrequencyDist(5) + 1
          If RunLengths(Base) = 6 Then TargetStrandFrequencyDist(6) =
TargetStrandFrequencyDist(6) + 1
          If RunLengths(Base) = 7 Then TargetStrandFrequencyDist(7) =
TargetStrandFrequencyDist(7) + 1
          If RunLengths(Base) = 8 Then TargetStrandFrequencyDist(8) =
TargetStrandFrequencyDist(8) + 1
          If RunLengths(Base) >= 9 Then TargetStrandFrequencyDist(9) =
TargetStrandFrequencyDist(9) + 1
          Next Base
Next Molecule
      For I = 1 To 9
      Worksheets("In Out").Cells(5 + I, 10).Value = TargetStrandFrequencyDist(I) 'copy to the
spreadsheet
      Next I
End Sub
Sub AnalyzeResults( )
Dim N As Integer
Dim TwentyFiveMer, TwentyFiveMerAccumulator As Integer
Dim LongestLength, ShortestLength As Integer
Dim TempSum, Min, Max As Integer
Dim AverageLength As Single
'----First we analyze the data about the degree of extension
For N = 1 To 1100        "clear the extension array.
      Extension(N) = 0
Next N
For Molecule = 1 To MoleculesMax
      N = 0
      For Base = 1 To 50
          If SynthesizedStrand(Molecule, Base) < > 0 Then N = Base
          'N = 1 'debug statement
      Next Base
      Extension(Molecule) = N
      'Worksheets("In Out").Range("C13").Value = Extension(N) 'debug statement
Next Molecule "---we now have an array of maximum lengths of each strand in Extension. We
can now compute...
'First we do the average:
TempSum = 0
For N = 1 To 1100
      TempSum = Extension(N) + TempSum '--grand total
Next N
AverageLength = TempSum / MoleculesMax
Worksheets("In Out").Range("D22").Value = AverageLength
'Now we find the Min and Max
Max = 0
Min = 50
For N = 1 To MoleculesMax
      If Max > Extension(N) Then Max = Max Else Max = Extension(N)
      If Min < Extension(N) Then Min = Min Else Min = Extension(N)
Next N
Worksheets("In Out").Range("D20").Value = Max
Worksheets("In Out").Range("D21").Value = Min
'Determine what fraction of molecules are more than 25 bases long
TwentyFiveMerAccumulator = 0
For N = 1 To MoleculesMax
      If Extension(N) > 24 Then TwentyFiveMerAccumulator = TwentyFiveMerAccumulator + 1
NextN
Worksheets("In Out").Range("E26").Value = TwentyFiveMerAccumulator / MoleculesMax
End Sub
Sub AnalyzeSynthesizedStrands( )
```

-continued

Source Code for Simulation of Short Cycle Sequencing

```
Dim CurrentBase As Integer
Dim BasesAhead As Integer
Dim N As Integer
Dim NumberedBases(51) As Integer
Dim RunLengths(51) As Integer
Dim TwoHitAccumulator, ThreePlusHitAccumulator, TwoHit, ThreeHit As Integer
TwoHitAccumulator = 0
ThreePlusHitAccumulator = 0
For I = 1 To 50
    NumberedBases(I) = 3
Next I
For Molecule = 1 To MoleculesMax 'Identify Changes among bases
    NumberedBases(1) = 1
    'Worksheets("Molecules").Cells(1 + Molecule * 4, 2).Value = NumberedBases(1) 'take this
out. For display only
        For Base = 2 To Extension(Molecule)
            If SynthesizedStrand(Molecule, Base − 1) < > SynthesizedStrand(Molecule, Base) Or
HL_Tracker(Molecule, Base − 1) < > HL_Tracker(Molecule, Base) Then
                NumberedBases(Base) = 1
            Else
                NumberedBases(Base) = 0
            End If
            'Worksheets("Molecules").Cells(1 + Molecule * 4, Base + 1).Value =
NumberedBases(Base) 'take this out. For display only
        Next Base
        '---------------compute run lengths
            '''But first we've got a boundary condition problem for the first base--we solve it here!!
        RunLengths(1) = 1
        'Worksheets("Molecules").Cells(1 + Molecule * 4, 2).Value = RunLengths(1)
        For Base = 2 To Extension(Molecule)
            If NumberedBases(Base) = 1 Then
                RunLengths(Base) = 1
            Else
                RunLengths(Base) = RunLengths(Base − 1) + 1
            End If
            'Worksheets("Molecules").Cells(1 + Molecule * 4, Base + 1).Value = RunLengths(Base)
        Next Base
        '----save only the terminal value of a run length
        For Base = 1 To Extension(Molecule)
            If RunLengths(Base + 1) > RunLengths(Base) Then RunLengths(Base) = 0
            'Worksheets("Molecules").Cells(1 + Molecule * 4, Base + 1).Value = RunLengths(Base)
        Next Base
        'Worksheets("Molecules").Cells(1 + Molecule * 4, 50 + 1).Value = RunLengths(Molecule)
'boundary condition
    TwoHit = 0
    ThreeHit = 0
    For Base = 1 To Extension(Molecule)
        If RunLengths(Base) = 2 Then
            Worksheets("Molecules").Cells(1 + Molecule * 4, Base + 1).Interior.ColorIndex =
Magenta
            TwoHit = 1
        End If
        If RunLengths(Base) > 2 Then
            Worksheets("Molecules").Cells(1 + Molecule * 4, Base + 1).Interior.ColorIndex = Cyan
            ThreeHit = 1
        End If
    Next Base
    '--Now determine what fraction of molecules have either 2 bases or 3+ base hits and report
results
    TwoHitAccumulator = TwoHitAccumulator + TwoHit
    ThreePlusHitAccumulator = ThreePlusHitAccumulator + ThreeHit
Next Molecule
Worksheets("In Out").Range("E24").Value = TwoHitAccumulator / MoleculesMax
Worksheets("In Out").Range("E25").Value = ThreePlusHitAccumulator / MoleculesMax
End Sub
Public Sub Main_Line( )
    Initialize
    '---Creates the new strands based on number of washes for varying degrees of completion per
cycle
    If MoleculesMax > 0 And WashCyclesMax > 0 Then
        CreateTargetStrands
        AnalyzeTargetStrands
        For WashCycles = 1 To WashCyclesMax 'Do the desired number of wash cycles
            Worksheets("Molecules").Range("I3").Value = WashCycles
            Synthesize
        Next WashCycles
        DrawSynthesizedStrands
```

| Source Code for Simulation of Short Cycle Sequencing |
|---|
| ``` 
        AnalyzeResults
        AnalyzeSynthesizedStrands
    End If
End Sub
``` |

EXAMPLE 3

FIG. 2 illustrates yet another simulated analysis of a number of target polynucleotides using short-cycle sequencing. The simulation was run using the program described in Examples 2a and 2b but using a larger number of target polynucleotides.

That is, in this simulation, the input values used were a cycle period of 0.8 half-lives, 60 repeats of the cycle, and 200 target polynucleotide strands. FIG. 2 illustrates the results obtained. Homopolymers stretches which occurred in the same simulated complementary strand are highlighted in magenta wherever nucleotides of the same base type were incorporated in a row, and in cyan wherever more than two nucleotides of the same base type were incorporated in a row.

The output values obtained were 48 incorporations in the longest extended complementary strand, 20 in the shortest, and 32.00 as the average number of incorporations for the 200 simulatedly extended complementary strands.

Further, the percentage of growing stands extended by two or more nucleotides in a homopolymer stretch was 78.5%; and the percentage of growing strands extended by three or more nucleotides in a homopolymer stretch was 4.0%. That is, using a cycle period of 0.8 half-lives resulted in 96.0% of the complementary strands being extended by two or less nucleotides in a homopolymer stretch per cycle of incorporation. Moreover, 95.5% of the 200 target polynucleotides of the simulation were extended by at least 25 incorporated nucleotides, while 100% were extended by at least 20 nucleotides. This illustrated that using a cycle period of 0.8 half-lives, and repeating the cycles 60 times, allows analysis of a 20 base sequence of 200 target polynucleotides.

EXAMPLE 4

This example demonstrates a method according to the invention in which a single nucleotide in a position in a nucleic acid sequence is identified. A template-bound primer is sequentially exposed first to a labeled nucleotide and then to an unlabeled nucleotide of the same type under conditions and in the presence of reagents that allow template-dependent primer extension. The template is analyzed in order to determine whether the first nucleotide is incorporated in the primer at the first position or not. If not, then the sequential exposure to labeled and unlabeled nucleotides is repeated using another type of nucleotide until one such nucleotide is determined to have incorporated at the first position. Once an incorporated nucleotide is determined, the identity of the nucleotide in the position in the nucleic acid sequence is identified as the complementary nucleotide.

EXAMPLE 5

In this example, a series of reactions are performed as described above in Example 1. A nucleic acid primer is hybridized to a target nucleic acid at a primer binding site in the target. The primer comprises a donor fluorophore. The hybridized primer is exposed to a first nucleotide comprising an acceptor fluorophore comprising a blocking moiety that, when incorporated into the primer, prevents further polymerization of the primer. The presence or absence of fluorescent emission from each of the donor and the acceptor is determined. A nucleotide that has been incorporated into the primer via complementary base pairing with the target is identified by the presence of fluorescent emission from the acceptor, and a sequence placeholder is identified as the absence of fluorescent emission from the donor and the acceptor. A sequence of the target nucleic acid is complied based upon the sequence of the incorporated nucleotides and the placeholders.

We claim:

1. A method for sequencing a nucleic acid template, the method comprising the steps of:
    (a) exposing a nucleic acid template hybridized to a primer to (i) a polymerase capable of catalyzing nucleotide addition to said primer, and (ii) a labeled nucleotide that is not a chain terminating nucleotide, under reaction conditions and for a time such that on average only one nucleotide is added to said primer by said polymerase to produce an extended primer incorporating said labeled nucleotide;
    (b) identifying said single labeled nucleotide incorporated in step (a);
    (c) neutralizing label in said single labeled nucleotide incorporated in step (a);
    (d) repeating steps (a), (b) and (c) at least once; and
    (e) determining a sequence of said template based upon the order of incorporation of said labeled nucleotides.

2. The method of claim 1, wherein said label is a detectable label.

3. The method of claim 2, wherein said detectable label is selected from the group consisting of cyanine, rhodamine, fluorescien, coumarin, BODIPY, alexa, and conjugated multi-dyes.

4. The method of claim 1, wherein said template is individually optically resolvable.

5. The method of claim 1, wherein said neutralizing step comprises cleaving said label from said nucleotide.

6. The method of claim 1, wherein in said exposing step said polymerase and/or said labeled nucleotide are present at concentrations such that a single labeled nucleotide is added to said primer.

7. The method of claim 1, further comprising the step of washing any unincorporated nucleotide prior to step b.

8. The method of claim 5, wherein said template is attached to a surface.

9. The method of claim 1, wherein said single labeled nucleotide is a deoxynucleotide selected from the group consisting of dATP, dTTP, dUTP, dCTP, and dGTP.

10. The method of claim 1, wherein said single-labeled nucleotide is a nucleotide analog.

11. The method of claim 1, wherein in said exposing step, the reaction conditions regulate the rate at which said single labeled nucleotide is added to said primer so that only one labeled nucleotide is added to said primer in each cycle.

12. A method for simultaneously sequencing plural nucleic acid templates, the method comprising the steps of:
(a) exposing simultaneously plural single molecule nucleic acid templates immobilized on a surface, each of which is hybridized to a primer, to (i) a polymerase capable of catalyzing nucleotide addition to said primers hybridized to said templates, and (ii) an optically detectable labeled nucleotide that is not a chain terminating nucleotide, under reaction conditions and for a time such that only one nucleotide is added to each said primer by said polymerase to produce plural extended primers incorporating said labeled nucleotide; and
(b) optically identifying which of said templates on said surface incorporated said single labeled nucleotide in step (a).

* * * * *

(12) INTER PARTES REEXAMINATION CERTIFICATE (464th)
United States Patent
Lapidus et al.

(10) Number: US 7,169,560 C1
(45) Certificate Issued: Oct. 4, 2012

(54) SHORT CYCLE METHODS FOR SEQUENCING POLYNUCLEOTIDES

(75) Inventors: Stanley N Lapidus, Bedford, NH (US); Philip Richard Buzby, Brockton, MA (US); Timothy Harris, Ocean County, NJ (US)

(73) Assignee: General Electric Capital Corporation, Bethesda, MD (US)

Reexamination Request:
No. 95/001,531, Jan. 27, 2011

Reexamination Certificate for:
Patent No.: 7,169,560
Issued: Jan. 30, 2007
Appl. No.: 10/852,482
Filed: May 24, 2004

Related U.S. Application Data

(60) Provisional application No. 60/546,277, filed on Feb. 19, 2004, provisional application No. 60/547,611, filed on Feb. 24, 2004, provisional application No. 60/519,862, filed on Nov. 12, 2003.

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search ........................ None
See application file for complete search history.

(56) References Cited

To view the complete listing of prior art documents cited during the proceeding for Reexamination Control Number 95/001,531, please refer to the USPTO's public Patent Application Information Retrieval (PAIR) system under the Display References tab.

*Primary Examiner* — Padma Shri Ponnaluri

(57) ABSTRACT

The invention provides methods for sequencing a polynucleotide comprising stopping an extension cycle in a sequence by synthesis reaction before the reaction has run to near or full completion.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-12 are cancelled.

\* \* \* \* \*